US009567652B2

(12) United States Patent
Virgin et al.

(10) Patent No.: US 9,567,652 B2
(45) Date of Patent: Feb. 14, 2017

(54) METHODS OF MURINE ASTROVIRUS DETECTION

(71) Applicant: Washington University, St. Louis, MO (US)

(72) Inventors: Herbert W. Virgin, St. Louis, MO (US); David Wang, St. Louis, MO (US); Joy Loh, St. Louis, MO (US); Thad Stappenbeck, St. Louis, MO (US); Guoyan Zhao, St. Louis, MO (US); Larissa Thackray, Columbia, IL (US); Christine Yokoyama, St. Louis, MO (US)

(73) Assignee: Washington University, Saint Louis, MO (US)

( * ) Notice: Subject to any disclaimer, the term of this patent is extended or adjusted under 35 U.S.C. 154(b) by 0 days.

(21) Appl. No.: 13/957,124

(22) Filed: Aug. 1, 2013

(65) Prior Publication Data
US 2014/0178855 A1 Jun. 26, 2014

Related U.S. Application Data

(60) Provisional application No. 61/678,346, filed on Aug. 1, 2012.

(51) Int. Cl.
*C12Q 1/70* (2006.01)
*C07K 14/005* (2006.01)
*C07K 16/10* (2006.01)
*C12N 7/00* (2006.01)

(52) U.S. Cl.
CPC ............ *C12Q 1/701* (2013.01); *C07K 14/005* (2013.01); *C07K 16/10* (2013.01); *C12N 7/00* (2013.01); *C12N 2770/12021* (2013.01); *C12N 2770/12022* (2013.01); *C12N 2770/12023* (2013.01)

(58) Field of Classification Search
None
See application file for complete search history.

(56) References Cited

U.S. PATENT DOCUMENTS

| 5,556,746 A | 9/1996 | Herrmann et al. |
| 2004/0031072 A1* | 2/2004 | La Rosa ............. C07K 14/415 800/278 |
| 2011/0045018 A1 | 2/2011 | Delwart et al. |

FOREIGN PATENT DOCUMENTS

| FR | WO 2009077611 A2 * | 6/2009 | ........... C07K 14/415 |
| WO | WO 03066879 A2 * | 8/2003 | ........... C07K 14/415 |
| WO | WO 2005040400 A2 * | 5/2005 | ........... C12Q 1/6827 |

OTHER PUBLICATIONS

GenBank Accession No. JF755422 (2011), 3 pages.*
Phan et al. PLos Pathog. 7(9), e1002218 (2011) + Supplemental Table 6.*
Royeula et al. Journal of Virological Methods 133, 14-19 (2006).*
GenBank Accession No. JQ408744 (2012), 2 pages, including revision history.*
Nolan et al. Nature Protocols 1, 1559-1582 (2006).*
De Benedictis, P., et al. "Astrovirus infections in humans and animals—molecular biology, genetic diversity, and interspecies transmissions" Infect Genet Evol. Oct. 2011;11(7):1529-44. Epub Aug. 5, 2011.
Mendez, E., et al. "Astroviruses" Fields Virology 5 Edition. Philadelphia: Lippincott Willliams & Wilkins 2007. 1:981-1000.
Walter, J.E., et al. "Molecular characterization of a novel recombinant strain of human astrovirus associated with gastroenteritis in children" Arch Virol. Dec. 2001;146(12):2357-67.
Phan, T.G., et a. "The fecal viral flora of wild rodents" PLoS Pathog. Sep. 2011;7(9):e1002218. Epub Sep. 1, 2011.
Blomstrom, A.L., et al. "Detection of a novel astrovirus in brain tissue of mink suffering from shaking mink syndrome by use of viral metagenomics" J Clin Microbiol. Dec. 2010;48(12):4392-6. Epub Oct. 6, 2010.
Quan, P.L., et al. "Astrovirus encephalitis in boy with X-linked agammaglobulinemia" Emerg Infect Dis. Jun. 2010;16 (6):918-25.
Lewis, T.L., et al. "An astrovirus frameshift signal induces ribosomal frameshifting in vitro" Arch Virol. 1995;140 (6):1127-35.
Lewis, T.L., et al. "Analysis of astrovirus serotype 1 RNA, identification of the viral RNA-dependent RNA polymerase motif, and expression of a viral structural protein" J Virol. Jan. 1994;68(1):77-83.
Jiang, B., et al. "RNA sequence of astrovirus: distinctive genomic organization and a putative retrovirus-like ribosomal frameshifting signal that directs the viral replicase synthesis" Proc Natl Acad Sci U S A. Nov. 15, 1993;90(22):10539-43.
Finkbeiner, S.R., et al. "Complete genome sequence of a highly divergent astrovirus isolated from a child with acute diarrhea" Virol J. Oct. 14, 2008;5:117.
Koci, M.D., et al. "Molecular characterization of an avian astrovirus" J Virol. Jul. 2000;74(13):6173-7.
Li, L., et al. "The fecal viral flora of California sea lions" J Virol. Oct. 2011;85(19):9909-17. Epub Jul. 27, 2011.
Reuter, G., et al. "Identification of a novel astrovirus in a domestic pig in Hungary" Arch Virol. Jan. 2011;156 (1):125-8. Epub Oct. 8, 2010.
Belliot, G., et al. "Outbreak of gastroenteritis in military recruits associated with serotype 3 astrovirus infection" J Med Virol. Feb. 1997;51(2):101-6.
Cunliffe, N.A., et al. "Detection and characterisation of human astroviruses in children with acute gastroenteritis in Blantyre, Malawi" J Med Virol. Aug. 2002;67(4):563-6.
Dennehy, P.H., et al. "A prospective case-control study of the role of astrovirus in acute diarrhea among hospitalized young children" J Infect Dis. Jul. 1, 2001;184(1):10-5. Epub May 31, 2001.
Finkbeiner, S.R., et al. "Identification of a novel astrovirus (astrovirus VA1) associated with an outbreak of acute gastroenteritis" J Virol. Oct. 2009;83(20):10836-9. Epub Aug. 12, 2009.
Gray, J.J., et al. "An outbreak of gastroenteritis in a home for the elderly associated with astrovirus type 1 and human calicivirus" J Med Virol. Dec. 1987;23(4):377-81.

(Continued)

*Primary Examiner* — Angela M Bertagna
(74) *Attorney, Agent, or Firm* — Zackson Law LLC; Saul L. Zackson

(57) ABSTRACT

Novel murine astroviruses, and methods of detecting the viruses are disclosed. Also disclosed are uses of the viruses and infected animals as model systems for discovery and development of vaccines and therapies for diseases caused by or associated with astrovirus infection, including human astrovirus-based diseases.

3 Claims, 11 Drawing Sheets
(3 of 11 Drawing Sheet(s) Filed in Color)

(56) References Cited

OTHER PUBLICATIONS

Grohmann, G.S., et al. "Enteric viruses and diarrhea in HIV-infected patients" Enteric Opportunistic Infections Working Group. N Engl J Med. Jul. 1, 1993;329(1):14-20.
Herrmann, J.E., et al. "Astroviruses as a cause of gastroenteritis in children" N Engl J Med. Jun. 20, 1991;324 (25):1757-60.
Jeong, H.S., et al. "Epidemiology of astrovirus infection in children" Korean J Pediatr. Mar. 2012;55(3):77-82. Epub Mar. 16, 2012.
Lewis, D.C., et al. "Outbreaks of astrovirus type 1 and rotavirus gastroenteritis in a geriatric in-patient population" J Hosp Infect. Jul. 1989;14(1):9-14.
Oishi, I., et al. "A large outbreak of acute gastroenteritis associated with astrovirus among students and teachers in Osaka, Japan" J Infect Dis. Aug. 1994;170(2):439-43.
Palombo, E.A., et al. "Annual incidence, serotype distribution, and genetic diversity of human astrovirus isolates from hospitalized children in Melbourne, Australia" J Clin Microbiol. Jul. 1996;34(7):1750-3.
Shastri, S., et al. Prevalence of astroviruses in a children's hospital. J Clin Microbiol. Sep. 1998;36(9):2571-4.
Wood, D.J., et al. "Chronic enteric virus infection in two T-cell immunodeficient children" J Med Virol. Apr. 1988;24 (4):435-44.
Koopmans, M.P., et al. "Age-stratified seroprevalence of neutralizing antibodies to astrovirus types 1 to 7 in humans in the Netherlands" Clin Diagn Lab Immunol. Jan. 1998;5(1):33-7.
Holtz, L.R., et al. "Astrovirus MLB2 viremia in febrile child" Emerg Infect Dis. Nov. 2011;17(11):2050-2.
Finkbeiner, S.R., et al. "Human stool contains a previously unrecognized diversity of novel astroviruses" Virol J. Oct. 8, 2009;6:161.
Thackray, L.B., et al. "Murine noroviruses comprising a single genogroup exhibit biological diversity despite limited sequence divergence" J Virol. Oct. 2007;81(19):10460-73. Epub Jul. 25, 2007.
Wobus, C.E., et al. "Murine norovirus: a model system to study norovirus biology and pathogenesis" J Virol. Jun. 2006;80(11):5104-12.
Coppo, P., et al. "Astrovirus enteritis in a chronic lymphocytic leukemia patient treated with fludarabine monophosphate" Ann Hematol. Jan. 2000;79(1):43-45.
Finkbeiner, S.R., et al. "Metagenomic analysis of human diarrhea: viral detection and discovery" PLoS Pathog. Feb. 29, 2008;4(2):e1000011.

\* cited by examiner

SEQUENCE LISTING

<160> NUMBER OF SEQ ID NOS: 12

<210> SEQ ID NO 1
<211> LENGTH: 6838
<212> TYPE: RNA
<213> ORGANISM: Mouse Astrovirus

<400> SEQUENCE: 1

```
ccaagaaaga ggcacuagug gcacuccugc ugcuaguaag ucugacaugg cccugcguaa      60
ggaguauacu ucccuugugg accaagcggu cgacgcuggg aauuaccugg cccgcugcca     120
guugccaacu acggcaauuc ugcugcugcg caauaugccu gaccacuauc cuaaccggcc     180
uuggucuguc cauucgaccc cccgccauuu ggucuauccc ucaacaacgg augauccaaa     240
gacgcggguu auaacagccu ccuccgucac aguggaggau gaauggguga ccuaugucug     300
gaccggcgcg cgcuggcagc agguggcaac ggccccugac uguggaaaaa cgauccuggu     360
cugugcccuc cugaacgaac auaagcggcu caaggaugag aaugcaagcc uuaaacuugc     420
caaggcgaau uuggagguug auaacaccac acugcgggug cgucagcgg  ccauuaccaa     480 cucggccccu cgccguucgc gccucccuug gauccuggca cucuuggcug ugcuuuucuc     540
ccuccucacg accucggcug ccuuugaaac cagcucuacc ucacggagcu augcccuga     600 ggauauugcu aggcacucug aggauugaa caccuuuauu gagaacgcuu ugaggugaa      660 ccacacacgc uccuacacag aguacaccua ccaacuguac gccacacaug cucagacuuu     720
cuuggaccgc auggccuuga cauuuaacac cuggcaagcu uaugauccgc acuucuuugc     780
gaaaacaccc uugcaaagug cgcuucgag uguccuccag uauguaacac ccuggacgug     840
ggagauagcc cuuacgggcu ugguauuggc gcucaugcua gcggaaaacu cuagcccuug     900
gucgcugcuc uaccuggccu gugcuacucu cacaaggacc cgcuuugccc ucuuggccgu     960
ggcgcccuuc cagacacgcu acacgacggc ugucaccguu gccgccucgg ugcucuacgc    1020
acucgacccc uuggucgcag uggcgugcca ggugcuacac cucuuucucc uggcaguggu    1080
ggggcucuuc auggaggaua ccuccuaugu ccaaaacuug aagggcgccu uccugcugcu    1140
augcgccuuc uucggccaug cccucugugc ccucuucgga gugagcucgg cgccagucac    1200
aacacuagcu guugccuggc ggaucuggcg gcuacucucu cgugccggaa caacaggcac    1260
cguggaggug cgcaaugaag aaggcaaggu ggucucaaaa cagaccacgc aacccaacuu    1320
ccucuuccgu uucaagcagg cguugaggag gaugagacaa cucagaacga cccagacccc    1380
ccuagcgcgc gucaauccug augcgcucug ccacaucagc guggccgggg cgaaaggcac    1440
```

```
uggcuucuuu ugugguaacu acgcugugac augugcacac guagucggga gugagacagu   1500
cgucaaccug ugcuauaaag gccguaacua ucaggcccca gugaagaaaa uccuggagca   1560
aaaggaugug gcacucauuc ccauaccugc ggggauaaca ccaccccgcu ugaagaucuc   1620
caagaagcac ugcugcgacu ggucugugu cugugccccc gacgugaug gugccuaccu    1680 aacugcugug acugagggu gcgagcauga uggucacuac uccuaugccu gcccgacgcg    1740
ggaugggaug ucuggcgcuc cucuguuaga cauagauggc cauguucuug ggauacacac   1800
uaacaacacu ggcuacacug guggugccca acgccucgac cuugaggaca uaguugaagc   1860
ccccaagcca auccaagc agcucgcccu cgagagggag auugaagaac ugaaaaagca    1920
gcuugcggcc cugcagccug aaccaccuag gccugagccc guggcugccc cucccucacc   1980
cguucagccc ggccccuag ugguuccaac uaccugcccc ccuccagccc caccggcacc    2040
aacuguggcc ccugcuccug uggccccag cccgguggcg cacuaugugg ucaaacccac    2100
ccaaauucca ccuaugcaac aaagccaac aacuagugau guggggauc uugugcgugc    2160 ggcaaugggu cgugagaugc aaauccugcg ggacgagcug aaccugauga ucaggcuaa    2220 agggaagacc aaacguggcc gugggaagaa gcauaccauc ggggcucgug uugguggccg    2280
ucgcagacag cgugggccug ccuucaccga ggaggaguac aaggagaugc uggaccaagg    2340
gauugacccc gaugagauca agcgccuagc cgaagaccuc ugggaggacc agacuggcuu    2400
cccggagugg agugacccug aguucucuga ugaggacgau gguggacac caaagaccca    2460 ugacuggcua gacuuugauu augaggauga uuuggaacaa acuuacgucc cuggucccug    2520
ggcccagaaa ugcaagauac cucucgucga cuacgucaag aagaucuuug acaaaggcuc    2580
cguugaugag auguuacaaa aucuugcccc ucuggagaag aagcucugua ggaaacaacu    2640
ugaggccguu cgccaggcaa aaacugauau cgagcucucu guugcacuug cgcuuugga    2700 ucgucgugcu gccgauguge gcaugcagcc cuuuacacca gggcuagagu auaaacaagc    2760 uguccaaaa aacgccaagg gccccgcaa gggggcaaaa gaucagggcu cgaagacugg    2820
aaagaacuaa ggcagccccc cuuucgccuc cugguacccc agccuuaccc uguugcugc    2880 agcuuacccc uggaccggcc caucuaugac aacgaugage cuaaagaucc acuucugggg    2940
guguugccac auguagacua ugagggcuaac uuugcaccaa caaccugggg aggcgcagcu    3000
uacgcgaaga guuucgagaa guucacguau gcucaaccug uggacuucga aaagcacuau    3060
ccuguagaaa ucaguucgc ugacugggcc uggcgagucc accacgcuua ccuggaaggc    3120 acucgggauau gccacaucau gucuacagag aaaaauaccg acucaaccc ugccuacccc    3180 aaaugccugg acuacuccac cgaggccgac uaccuagagg aacauggcug ggagcccuau    3240
gucaacgcuu uccgugccau ugacccgggg gagcggcccc agguucucug guccucuuc    3300 uugaagaagg agauucucaa acaagagaag auucgcgauu cagacauucg ucagauuguc    3360
uguucagauc ccaucuaugc gcggaucgga gcuugcuucg aacaacauca aaaccaucuc    3420
augaagcaaa aaacagagac ccauuccggg caauguggcu ggugcccccu aagggggc    3480 uuugaggcaa ugugccaccg ucuugccucu aagcagggug ucuuuggga auuugacugg    3540 acacgcuuug auggaacaau ccccguacaa cucuuccgca ggauaaagaa gcuccgcugg    3600
uccaugauuu gucccgaaca ucagcagcgc uacgggcaca uguaccagug guauguuaac    3660
aaucucuugc accgcuacac cgucugcccc ucaggugagg ugaccaucca aacucgugcc    3720
aaccccucag ggcaaaaucuc aacaacaaug gauaacaaca ugguuaacua cuggcuucag    3780
```

```
gcauuugagu ucugcuacuu cuuuggcccu gauaaagauc ucuggcggca guaugauacu      3840
gucugcuaug gugaugaccg gcuuacgcgc uacccugugc uaccacccca uuacaucgag      3900
cggguggucg ccauguacaa ggacaucuuu ggcaugaggg uuaaaccuga aaaggugcgc      3960
guuagugaca cccugguugg ucucaccuuu uguggcuuua gauagggga gcacuauuug       4020 cccuauccug cacaggaaga caaacucuuu gccggccucg uccggccagu gaggaaauug      4080
gcugacuuua aaacacucca ugggaaacuc uugagccugc agcuucugau gcacuuccac      4140
ccuccgaguc ccuuuaagga cuacuuggag augugcuugg caaacaccgc caaguacugc      4200
ccggaacuuc cggcgcgguu uucagagcgu cagauggaca agcuuggag gggaggacca      4260 aaagcuguuc auggcuaagg ccaaacaaca acagaaaaau gccacgaccg ucacuacuac      4320 aacugcacu ggucgcagua gucggcgguc ucgcaggcgc ucuguacggc gccgcgcugc       4380
aggcccuucu aaccccccaa caaagacaac aacuguucgg acuguuuuc gccgcacugc       4440 ccggccucgc ggugauccgcc gcaggaguag gaaugcucag cggcaggcuc ucgcgaggu      4500 uguucagacg guuacggcga cccucggaac gguuggcgcg aaccagggca ucaggucga      4560 gcuugagaug gcagcgcucc ucaacccagc gcuaauuaaa gaaacaacug gcucaaacgc      4620
cuucggacca cuccagaugu augccuccac gcaugccaug uggaaagugg auaggcucac      4680
acucaagcuc accccucugg ucggcgccuc ugcuguuucc gguacagcgg uccgugccuc      4740
acugaauaug caucgggc ccgccgcgcc cgccuggca gccuugggcg cgcggaagca        4800 ugguggacacc aauccuggguc ggccggcuuc cuucacccuc acagccgccg auguaccugg   4860 cccccaagcag gguuggguucu uuacuaauac uaagcaggag gccggcuuua cagucggcgg   4920
ggccauugag auccauaccc ucggcaagac gaugucaacc uaccagaacu cagccuauac     4980
gggcccacuc uuucuugccg aggucacagg uaccuggagg uuuaagaacu acgagccca     5040 gcccggcuug cucaaccucc ucaagaccga gguuaaagag ccugcgggca cugugaaggu     5100
acacuccaaa ccuggagaac cugucacgcu cuccaucccu caagcaggga ccuuugcuggg    5160 ccuagagagg cuaaauccaa cagccucggc cacaccaggu gagaucaucu gggagguagu     5220
ggauuccgcu gcgaaugcgg ucuccggcuu gcuccucaa cccuggcagu ggcuuuuuaa      5280
aggcggcugg uucuucccuga aaagaauugc caaccggaaa ccuguuggug ccgccagugu    5340
ggcgggugaa ccgauggag gugaagugac uuuccgcgug uacgccagua ucgcggaugc      5400
ccagaaugau gugcccugua uugccagcuc ggcggccucc acucaauccca uacagacgga   5460 gggucucaag auccccagg ugacuccugg gaccauugu augccugaaa cugcaguagc       5520
cacacacaac auggcuccac cacccgaguc cggacccuau accaucaag ggcccaccuu      5580 ggaggcugcu gcuccuuugc acgccccaa guauacacag uggacuauug uagaugcugg     5640
uaccucccag gagcaggccc gccugcgcuc cgggguggu ccagcagagc agaccucagc     5700
cuggucgagc uguacucugg agcucccagg caccuuccuc cagaauaugu augaugauuga  5760 uccccgugau auugcagccg guaccuuucc caucaaucac uggaacguga gcaccucgcg    5820
gcucacgcgg cuuggcaccg ccuacgguug caaucaggcg cgggccgca ccaugggga     5880 gggagucccg caugugguua ucuacuccac uucgugucuc uggauggccg acguuuccac    5940
aggguggaac uaugacaacu ucuccgcugc caucuggaau cccauagugg uagcgggcc     6000 aaacgucau gggacugaac aggcauuccc ucucacccgg gaacccuca acuggcccgg      6060 gggcgauagg aaaucgcuggc ccuaccgcaa ccagauugaa aagggucacu gguaugugac    6120
cuucuggacu caguacgauc cugaugagug ggucugguug gaugaguucc aucuccaguu    6180
```

```
caccuugcaa ccgggcacgc acacccccac ugaaaaccau acugggaug uaacagcaga    6240 cagcuuaggu acuggccucu ggggccuccg ggaccuugug uucuacccaa uagguaccca    6300
gcccaggaua gugauaccaa acacugggcc uaccagcucc caugugaccu ucgaccuccc    6360
cccgggugag ggcgaagauu acucuacaga ugaggaaggc gaguccgaug agggagcuga    6420
ggaugaugaa ggaaauccccc uugaauuuga ccacccauua acggcgauc ucucgcaacc    6480 ccccgccgcc guccugaaag aucugaccua caaggggcgu aaucucgcca augaauugug    6540
gaguacgggg gugccagaug cgaaggccug gcuggcggga cagaccaucg acccgucgcc    6600
auccuuucgc cgcuggcgag agacuuuuca aaaagcgcuc cagcggugug uagcacccu    6660 ggaagcgcau gagcucgcua cuagcgaguu ccuugcucaa agagaaagcc gcggccacgc    6720
cgaguaggau cgagggguaca gcuuucuccc cugcuuuucu gcuucuuucu gugcuuuggu    6780
guuacuuuag ggugauauaa uuggcauaaa aauuggcaaa aaaaaaaaaa aaaaaaa      6838

<210> SEQ ID NO 2
<211> LENGTH: 6827
<212> TYPE: RNA
<213> ORGANISM: Mouse Astrovirus

<400> SEQUENCE: 2
ccaagaaaga ggcacuagug gcacuccugc ugcuaguaag ucugacaugg cccugcguaa      60
ggaguauacu ucccuugugg accaagcggu cgacgccggg aacuaucugg cccgcugcca     120
guugccaacu acggcaauuc ugcuguugcg caacaugccc gaccaccacu ccaaucggcc     180
cuggucuguc cauucaacuc cccgccacuu ggucuauccc ucaacaacgg acgacccaag     240
gaugcggguu auaacagccu ccuccguaac aguggaggau gaaugggguga ccaugccug     300 gaccggugcg cgcuggcagc agguggcaac ggccccugau gcgggaaga cgauccuggu     360 cugcgcccuc cugaacgaac auaagcggcu caaggaugag aaugcaagcc ucaaacuugc     420
caaggcgaac uuggagguug auaacaccac acuacggguug gcgucggcgg ccaucaccaa     480
cccggccccu cgccgcucgc gccuccccug gauccuggca cucuuggcug ucuucuucuc     540
ccuccucacg accucggcug ccuuugaaac cagcucuacc ucgcggaguu augcccccuga     600 ggauauugcu aggcacucug aggacuugaa caccuuuauu gagaacgcuu ugagggguaaa     660 ccauacgacg uccuacacgg aguacaccua ccaacuguau uccacacaug cucagacuuu     720
cuuagaucgc auggccuuga cauucaacac cuggcaagcc uaugauccgc acuucuuugu     780
gaaaacaccu cugcaaagug cgcuucgag ugucccccag uauguaacac ccuggacgug     840
ggagauagcc cuuacgggcu uggugcuggc gcucaugcua gcagagaaua cuagcccuug     900
ggcgcugcuc uaccuagccu gcgcuacucu cacaaggacc cgcuuugccc ucuuggccgu     960
ggcgcccuuc cagacacgcu acacgacggc uguaacuauu gccgucucgg ugcucuacgc    1020
acucgacccc uuggucgcug uggcgugcc gguguaca cucuuuucucu uggcaguggu    1080 ggggcucuuc auggaggaca ccuccuaugu ccaaaacuug aagggcgccu uucugcugcu    1140
augcgccuuc uuuggccacg cccuugccgc ccuuucgga gugagcucgg cgccagucac    1200
gacacuggcu gucgucuggc gaaucuggcg gcuacucucu cgugccggaa caacaggcac    1260 ugugggaggug cgcaaugaag aaggcaaggu ggucucaaaa cagaccacac aaccccaacuu    1320 ccucuuccgc uucaagcagg cguugaggag gaugagacaa cuuagaacga cccagacccc    1380
ccuggcacgc gucaauccug augcgcucug ccacgucagc guaaccgggg cgaagggcac    1440
```

```
uggcuucuuc uguggvaacu augcugugac augcgcacac guaguuggga gugagacagu    1500
ugucaaccug ugcuauaaag gccauaacua ccaggcccca gugaagaaaa uccuggcgca    1560
uaaggaugug gcacucauuu ccauaccaac ggggcuaaca ccaccccgcu ugaagaucuc    1620
uaggaagcac ugcugcgacu gggucugcgu uugugccccc gacgvgaug cgccuaccu      1680 aaccgcugua acugagggu gcgagcauga uggucacuac uccacgucu gcccgacgcg      1740 ggaugggaug ucuggugcuc cucugcuaga cauagauggc caugccuug ggauacauac     1800 caacaauacu ggcuauacug guggugccca acgccucgac cuugaugaua uaguugagcc    1860
ccccaagcca aguccaggc agcucgcccu cgaggcggag guugaaaacc ugagaaaaca     1920
gcucgaaagu cugcggucug aacccuuuag gccugagucc guggcugccc ucucuucaac    1980
cgugcagccc ggccccccuag ugguccaac uaccugcccu ccccagccc caccggcacc     2040 aacugugguc ccuguucccg uggccccuag cccuggguu aaacccaccc aaacuccacc     2100
uaugcaacaa agcuugacaa cuagugaugu ggugaucuu gucgcgcgg caaugggucg      2160 ugagaugcaa auccugcggg acgagcugaa ccugaugaau caggcuaaag ggaagacuaa    2220
gcguggccgu gggaagaagc acacuauucg ggcucugugu uggugccgcc gcaaacagcg    2280
uggcccugcc uucacugaag aggaguauaa ggagaugcug gaccaaggga uugaucccga    2340
ugagaucaag cgucuagcug aagaccucug gaggaccag acugguucc cagagaggag      2400 ugauccgag uucucugaug aggacgaugg cuggacacca aaaacucaug auuggcuaga     2460 cuuugauua gaggaugacu ggaacaaac ccaugucccu gguccuggg cccagaaaug       2520 caagauaccu cucgucgacu augucaagaa gaucuuugac agagcucug uugaugagau     2580 guuacaaaau cuugcccccc uggagaagaa gcucuguagg aaacagcucg aggccgvccg    2640
ccaggcaaac acugauaucg agcuuuccgu ugcacuggc gccuuggauc gucgugcugc     2700
cgaugucggc augcagcccu uuacaccagg ccuagaguac aaacaggcug uuccaaaaaa    2760
cgccaagggc ccccgcaagg gggcaaaaga ucagggcucg aagacuggaa agaacugagg    2820 cagcccccu uucgccuccu gguaccccag ccuuacccug uugucugcag cuuaccccug     2880
gaccggccca ucuaugacaa cgaugagccc aaagauccgc uucgggggu guugccacau    2940 guggacuacg agggvaauuu ugcaccaaca accuggggag gcgcagccua cgcgaagagu    3000
uucgagaagu ucacauacgc ucaaccugug gacuucgaaa agcacuaucc uguagaaacu    3060
caguucgcug acugggccug gcgagccau acgccuauc uggaaggcac ucgggucugu     3120
cacaucaugu cuacagagaa aaauaccgac ucgaccccg ccuacccaa augccuggac      3180 uacuccaccg aggccgacua ccuggaggaa cauggcuggg agcccaugu caacgccuuc    3240 cgugccaucg auuccgggga gcggcccag guucucuggu uccucuucuu gaagaaggag    3300
auucucaaac aagagaagau ucgcgacuca gacauucguc agauugucug cucagauccc   3360
aucuaugcgc ggaucggagc uugcuucgaa caacaucaaa aucaucucau gaagcaaaaa    3420
acagagaccc acuccgggca augugggugg ugccccuga agggggcuu ugaggcaaug     3480 ugccaucguc uugccucuaa gcagggvguc uuuguggaau ugacuggac acgcuuugau    3540 ggaacaaucc cuguacaacu cuuccgcagg auaaagaagc uucgcugguc cauggvuugc   3600
cccgaacauc agcagcgcua cgggcacaug uaccgguggu auguuaacaa ccuccugcac   3660
cgcuacaccg ugcugcccuc aggcgaggug accauccaaa cucgggcaa ccccucaggg    3720 caaaucucaa caacaaugga uaauaauaug guuaacuacu ggcuucaggc auuugaguuc    3780
ugcuacuucu uuggccccaa uaaggaucuc uggcggcagu augauacugu cugcuauggu    3840
```

-continued

```
gaugaccggc ucacgcgcua cccugugcua ccgccccacu acaucgagcg ggugguccgcc      3900 auguauaagg acaucuuugg caugugggu aaaccugaaa aggugcgcgu uagugacacu        3960 cgguugguc ucaccuucug uggcuuuaga auaggggagc acuauuugcc uuauccugca        4020
caggaagaua aacucuuugc cggccucguc cggccaguga ggaaauuggc ugacuucaaa       4080
acacuccaug ggaaacucuu gagccugcag cuucugaugc acuucaucc uccgagucccc      4140 uucaaggacu acuuggagau gugccuggca aacaccgcca aguacugccc ggaacuuccg       4200 gcgcgguuu cagagcguca gauggacaag cuuggaggg gaggaccaaa agcuguucau        4260
ggcuaaggcc aaacaaccac agaaaaaugc cacgaccguc acuacuacaa cugucucugg      4320
uggcaguagu cggcggucuc gcaggcgcuc uguacggcgc cgcgcuacag gcucuucuaa      4380 cccccaaca aagacaacaa cuguuucgac uguuuucgc cgcaauaccc ggccucgcgg        4440
uaaucgccgc aggaguagga augcucagcg gcaggcuccu cgcgagguug uccagacggu      4500
uacgcgaccc cucggaacgg uuggcgcgaa ccagggcgau caggucgagc uugagauggc      4560
agcgcuccuc agcccagcgc ugauuaagga aacaacuggu caaacgccu uugggccacu       4620 ccagauguau gccuccacgc augccaugug gagagugggga aggcucacac ucaggcucac    4680 ccccuggu ggcgccucug ccguuuccgg cacagcaguc cgugccucac ugaacaugac       4740
aucugggccc gcugcgcccg ccuggucagc cuugggcgcg cggaagcaug uggauaccaa     4800
cccuggucgg ccggcuuccu ucacccuuac agccgccgau guaccuggcc caagcaggg      4860 cugguuccuu acuaacacua agcaggaugc cggcuuuuca gucggcgggg ccauugagau      4920
acacacccuc ggcaagacga ugucaacuua ucagaauaaa gccuaugaug gcccacuuuu      4980
ucuugccgag ucacgggca ccuggagguu aagaacuau gagccccagc ccggcaugcu        5040
caaccuccuc aagaccgagg ucaaggagcc cgcggguacu gugaagaucc acuccaagcc      5100
uggagaaccu gucacgcucu ccaucccuga agcaggacc uuugcuggcc uagagaggcu       5160
aaauccaaca gccucggcca cgccagguga gaucaucugg gagguagugg auuccgccgc      5220
gaaggcgguu uccggccuugc uuccucaacc cuggcagugg cucuuuaaag gcggcugguu    5280
uuuccugaaa agaauugcca accggaaacc uguuggcgcu gccagugugg cgggugaacc     5340
ugauggaggu gaggugaccu uccgcguaua cgcuaguauc gcggaugccc agaaugaugu     5400
acccuguauc gccagcucgg cggccucuac ucaauccaua cagacggagg ggcucaagau     5460 ucccaggug acuccugggagcauuggcau gccugaaacu gcaauugcca cacauaauau       5520 gguccacca cccgaguccg gaccucacua cuaucagggg cccacccugg aggcugcuau      5580
ucccuugcgc ggcccaagu auacacagug gauucuugug gaugccggac gcucccagga     5640 aucgcccgc cuccauuccg gggugguccc ggcagagcag accucggccu ggucgagcug     5700
uaccuuggaa cucccaggca cuuccuccca gaauaugcau gagauugauc cccgugaugu     5760
ugcagccggu accuuucca ucaacuacug gaaugcgagc accucgacgc ucacgcggcu     5820
cgguaccgcc uacgguugca aucaagcgcg ggcacgcacc uauggggagg gagucccgca    5880
uguggucauc uccaccaccu cugucccucu gagggccgau gucccgaag ggguggaacua    5940 ugacaacuuu uagcugcca ucuggaaucc uauuguggag gcugggccua auguccaugg     6000
aaccgaacag ggcaugccuc uuacccgugg cacucucaac uggcccggag gcgauaggaa    6060
ucgcuggccc uaccgcaacc agauugagga ggucgcugg uacgugaccu ucuggacuca      6120
guacgauccu gaugagugggg ucugguugga ugaguuccau cuucaguuca ccuugcagcc    6180
```

| | |
|---|---:|
| gggcacgcau gccccuaccg auaaccauca cugggauaua acaacagaua gucuagguac | 6240 |
| uggccucugg ggccuccggg aucuuguguu cucccaaua ggguucagc ccaggauagu | 6300 |
| gauaccccc acugggccua ccagcucccg ugugaccuuc gaccucccu cgggugagga | 6360 |
| cgaugaguac uacacagaug aggaaggcga guccgaugag ggagcugagg augaugaagg | 6420 |
| accccccuu gaauuugacc acccauuaga cggcgaucuc ucgcaacccc ccgccgccgu | 6480 |
| cuugaaagau cugaccuaca aggggcgcaa ucucgccaau gaguugugga guacggggu | 6540 |
| gccagaugcg aaggccuggc uggcgggaca gaccguugac ccgucgccau ccuuucgccg | 6600 |
| cuggcgggag acuuuucaaa aagcgcucca gcgugugug aaaccccugg aagcgcguga | 6660 |
| gcucgcuacu agcgaguucc uugcucaaag agaaagccgc ggccacgccg aguaggaucg | 6720 |
| aggguacagc uuucucccu ugcuuuucug cuucuuucug ugcuuuggug uuacuuuagg | 6780 |
| gugauauaau uggcauaaaa auuggcaaaa aaaaaaaaaa aaaaaa | 6827 |

```
<210> SEQ ID NO 3
<211> LENGTH: 2610
<212> TYPE: RNA
<213> ORGANISM: Mouse Astrovirus

<400> SEQUENCE: 3
```

| | |
|---|---:|
| cuuuggaggg guggaccaaa agcuguucau ggcuaaggcc aaacaacaac agaaaaaugc | 60 |
| uacgaccguc accacuacaa cuguuucugg uggcaguggu cggcggcucu gcaggcgcgc | 120 |
| uguacggcgc cgcgcugcag gcucuucuaa ccccucaaca aagacaacaa cuguucggac | 180 |
| uguuuuucgc cgcaauaccc ggccucgcgg uaaucgccgc aggaguagga augcucagcg | 240 |
| gcagacuccu cgcgagguug uccagacggu acggcgacc cucggaacgg uuggcgcgaa | 300 |
| ccagggcgau caggucgagc uugagauggc agcgcuccuc agcccagcgc ugaucaagga | 360 |
| aacaacuggc ucaaaugcau uugguccacu acagauguau gccuccacgc augccaugug | 420 |
| gaggguggau aggcucacac ucaagcucac ccccuugguc ggcgccuccg ccgucuccgg | 480 |
| uacagcaguu cgugccucac ugaauaugac aucaggaccc gcugcgcccg ccuggucagc | 540 |
| ucugggcgcg cggaagcacg uggauaccaa cccuggucgg ucggccuccu ucacccucac | 600 |
| agccgccgac aucccuggcc cuaagcaagg uugguuccuc acuaacacca agcaagacgc | 660 |
| cggcuucuca gucggcgggg ccauugagau ccauacucuc ggcaagacaa ugucaaaccua | 720 |
| ccagaaugcg cccuacaccg gcccacucuu ucuugccgag ucacaggca ccuggagguu | 780 |
| uaagaacuau gagccccagc cuggcaugcu uaaccuccuc aagaccgagg uuaaagagcc | 840 |
| ugcgggcacu gugaaaguac acucaaagcc cggggagccu gucacacucu cuauuccuga | 900 |
| agcagggacc uuugccggcc uugagaggcu aaauccaaca gcuucggcca cgccgggguga | 960 |
| gaucaucugg gagguggugg acuccgccgc gaaugcgguc uccggacuac ucccucaacc | 1020 |
| cuggcagugg cucuuuaaag gcggcugguu cuuccugaaa aggauugcca accggaaacc | 1080 |
| gguuggugcu gcuacuguga cgggugaacc ugauggaggu gaaguuaccu uccgcgucua | 1140 |
| ugccagcauc gcggaugccc agaaugaugu ccuugcauu gcuuccucgc aggccucuac | 1200 |
| ucaauccaua cagacgcagg ggcuuaagau cucucaagug acuccuggga ccauuggcau | 1260 |
| gcccgaaacc gcgauugcca cccauaauau gguccacca ccugagucug acccuacua | 1320 |
| cuaucagggg cccacccugg aggcugcugc uccccgaaaa gcccaaauu acacacagug | 1380 |
| gauacuugug gacgcugggg cucccagga ggggccucgc cuacacuccg ggugguucc | 1440 |
| agcagagcag accucagccu ggucgagcug caccuuggag cucccaggca ccuuccuccca | 1500 |

```
gaacaugcau gagauugacc cccgugacgu ugcagccggu accuuuccca ucaaucacug    1560
gaaugcgaac acuucggugc ucacgcggcu uggcaccgcc uacgguugca accaagcgcg    1620
gguucgcacc uccggggaag ucacgcuggu uaucuccacc acuucuguuc ucuggagggc    1680
cgaugucucc auagggugga acuaugacaa cuuccuagcu gccaucuggu gccccauugu    1740
gguggcuggg ccuggugucc auggaacuga acagggcaug ccucuuaccc ggggcacucu    1800
caacuggccc gggggcgaua ggaaucgcug gcccuaccgu aaccagauug gagagggucu    1860
cugguaugug accuucugga cucaguacga uccugaugag ugggucuggu uggacgacuu    1920
ccaccuccag uuccaccuug caaccgggca gcauacccc acugauaacc accgcuggga     1980
uauaacaaca gauagcuugg gcacuggccu cggggccuc cgggaccuug uguucuaccc     2040
aauagguguu cagcccagga uagugauacc acccacuggg ccuaccagcu cccguguggu    2100
cuucgaccuc cccucggguga aggacgauga guacuacaca gaugaggaag cgaguccga    2160 ugagggagcu gaggaugaug aaggaaaccc ccuugauuuu gaccacccau uagacggcga    2220
ucucucgcaa cccccccgccg ccgucuugaa agaucugacu uauaaggggc guaaucucgc   2280
caaugaguug uggaguacgg gggugccaga ugcgaaggcc ugguuggcgg acaagccgu     2340 ugacccgucg ccauccuuuc gccgcuggcg ggagaccuau caaaaagcgc uccagcgugg    2400
uuugaaaccc cuggaagcgc gugagcucgc uacuagcgag uuccuugcuc aaagagaaag    2460
ccgcggccac gccgaguagg aucgagggua cagcuuucuc cccugcuuuu cugcuucuuu    2520
cugugcuucu gguguuacuu agggugauua uaauuggcau aaaaauuggc aaaaaaaaaa    2580
aaaaaaaaaa aaaaaaaaaa aaaaaaaaaa                                     2610

<210> SEQ ID NO 4
<211> LENGTH: 2616
<212> TYPE: RNA
<213> ORGANISM: Mouse Astrovirus

<400> SEQUENCE: 4
cuuuggaggg guggaccaaa agcuguucau ggcuaaggcc aaacaacaac agaaaaaugc      60
cacgaccguc accacuacaa cuguuucugg uggcaguggu cggcggucuc gcaggcgcgc    120
uguacggcgc cgcgcugcag gcucuucuaa ccccucaaca aagacaacaa cuguucggac    180
uguuuuucgc cgcaauaccc ggccucgcgg uaaucgccgc aggaguagga augcucagcg    240
gcagacuccu cgcgagguug uccagacggu uacggcgacc cucggaacgg uuggcgcgaa    300
ccagggcgau caggucgagc uugagauggc agcgcuccuc agcccagcgc ugaucaagga    360
aacaacuggc ucaaaugcuu uuggccacu acagauguau gccuccacgc augccaugug    420
gaggguggau aggcucacac ucaagcucac cccccuuggu cggcgccuccg ccgucuccgg    480 cacagcaguu cgugccucac ugaauaugac aucaggaccc gcugcgcccg ccuggucagc    540
ucugggcgcg cggaagcacg uggauaccaa cccuggucgg ucggccucuu caccccucac    600
agccgccgac aucccuggcc cuaagcaagg uugguuccuc acuaacacca gcaagacgc    660 cggcuucuca gucggcgggg ccauugagau ucauacucuc ggcaagacaa ugucaaccua    720
ccagaaugcg cccuauaccg gcccacucuu ucuugccgag ucacaggua ccuggaggu     780 uaagaacuau gagccccagc cuggcaugcu aaccuccuc aagaccgagg uuaaagagcc     840
ugcgggcacu gugaaaguac auucaaagcc cggggagccu ucacacuuu cuauuccuga    900 agcagggacc uuugccggcc uugagaggcu aaauccaaca gccucggcca cgccggguga   960
```

```
gaucaucugg gaggugguqg acuccgccgc gaaugcgguc uccggacuac ucccucaacc    1020
cuggcagugg cucuuuaaag gcggcugguu cuuccugaaa aggauugcca accggaaacc    1080
gguuggugcu gcuacugugg cgggugaacc ugauggaggu gaaguuaccu uccgcgucua    1140
ugccagcauc gcggaugccc agaaugaugu uccuugcauu gccucccgc aggccucuac    1200 ucaauccaua cagacgcagg ggcuuaagau cucucaagug acuccuggga ccauuggcau    1260
gcccgaaacc gcgauugcca cccauaauau ggucccacca ccugagucug gacccuauua    1320
cuaucagggg cccacccugg aggcugcugc uccccugaaa gccccaaaau acacacagug    1380
gauacuugug gacgcuggga cucccaggag ggggccucgc uuacacuccg ggugguucc     1440 agcagggcag accucagccu ggucgagcug caccuuggag cucccaggca ccuucuuca    1500 gaacaugcau gagauugauc cccgugaugu ugcagcuggc acuuucccca ucaaccacug    1560
gaacgugcgc accucgacgc uuacgcggcu uggcaucgcc uauggcugua aucaggcgcg    1620
gguccgcacc uauggggaag ggucccgca uguggucauu uccaccaccu cugugcucug     1680
gagggccgau gucuccgaag gcuggaacua ugacaacuuu cuugcugcca ucuggaaucc    1740
cauuguggag gcugggcccu ccacccaugg aacugaacag ggugugccuc uuacccgggg    1800
cacucucaac uggcccgggg gugauagaaa ucgcuggccc uaccgcaacc agguugagga    1860
aggucacugg uacgugaccu ucuggacuca guacgauccu gaugaguggg ucugguugga    1920
ugaguucaau cuccaguuca ccuugcagcc cggcaaccac accccuacug cuaaccacca    1980 cuggauauaua acaacagaua gcuuaggcac uggccucugg ggccuccggg accuugucuu    2040
cuauccaaua gguguccagc ccaggauagu gauaccgccu acugggccua cuagcucccg     2100
ugugaccuuc gaccucccu cgggugagga cgaugaguau uacacagaug aggaaggcga     2160
guccgaugag ggagcucagg augaugaagg gaauccccuu gaauuugacc auccauuaga    2220
cggcgaucuc ucgcaacccc ccgccgccgu ccugaaagau cuaaccuaca aggggcaaaa    2280
ucucgccaau gaguugugga guacgggggu gccagaugcg aaggccuggc uggcggggca    2340
gacuguugac ccgucgccau ccuuucgccg cuggcgggag accuucaaa aagcgcucca    2400 gcguggugua aagccccugg aagcgcgaga cucgccacc agcgaguucc uugcucaaag    2460
agaaagccgc ggccacgccg aguaggaucg agggнucagc uuucucuccc cgcuuuucug    2520
cuccuuuucu gugcuuuugg uguuacuuua gggugauaua auuggcauaa aaauuggcaa    2580 aaaaaaaaa aaaaaaaa aaaaaaaa aaaaa                                   2616

<210> SEQ ID NO 5
<211> LENGTH: 34
<212> TYPE: RNA
<213> ORGANISM: Artificial Sequence
<220> FEATURE:
<223> OTHER INFORMATION: Artificial Oligonucleotide

<400> SEQUENCE: 5
cuuuggaggg gaggaccaaa agcucuucau gggc                               34

<210> SEQ ID NO 6
<211> LENGTH: 26
<212> TYPE: DNA
<213> ORGANISM: Artificial Sequence
<220> FEATURE:
<223> OTHER INFORMATION: Artificial Oligonucleotide

<400> SEQUENCE: 6
ccaagaaaga ggcactagtg gcactc                                        26
```

```
<210> SEQ ID NO 7
<211> LENGTH: 50
<212> TYPE: DNA
<213> ORGANISM: Artificial Sequence
<220> FEATURE:
<223> OTHER INFORMATION: Artificial Oligonucleotide

<400> SEQUENCE: 7 gtttttttt tttttttttt ttgccaattt ttatgccaat tatatcaccc        50

<210> SEQ ID NO 8
<211> LENGTH: 20
<212> TYPE: DNA
<213> ORGANISM: Artificial Sequence
<220> FEATURE:
<223> OTHER INFORMATION: Artificial Oligonucleotide

<400> SEQUENCE: 8
tacatcgagc gggtggtcgc                                         20

<210> SEQ ID NO 9
<211> LENGTH: 24
<212> TYPE: DNA
<213> ORGANISM: Artificial Sequence
<220> FEATURE:
<223> OTHER INFORMATION: Artificial Oligonucleotide

<400> SEQUENCE: 9
gtgtcactaa cgcgcacctt ttca                                    24

<210> SEQ ID NO 10
<211> LENGTH: 17
<212> TYPE: DNA
<213> ORGANISM: Artificial Sequence
<220> FEATURE:
<223> OTHER INFORMATION: Artificial Oligonucleotide

<400> SEQUENCE: 10
tttggcatgt gggttaa                                            17

<210> SEQ ID NO 11
<211> LENGTH: 15
<212> TYPE: PRT
<213> ORGANISM: Artificial Sequence
<220> FEATURE:
<223> OTHER INFORMATION: Artificial OligoPeptide

<400> SEQUENCE: 11

Cys Gly Gly Asp Arg Asn Arg Trp Pro Tyr Arg Asn Gln Ile Glu
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Artificial OligoPeptide

<400> SEQUENCE: 12

Cys Ser Glu Phe Leu Ala Gln Arg Glu Ser Arg Gly His Ala Glu
1               5                   10                  15
```

METHODS OF MURINE ASTROVIRUS DETECTION

RELATED APPLICATION DATA

This application claims the benefit of U.S. Provisional Application No. 61/678,346, filed Aug. 1, 2012. The disclosure of U.S. Provisional Application No. 61/678,346 is incorporated herein by reference in its entirety.

GOVERNMENT RIGHTS

This invention was made with government support under AI054483, AI057160 and AI084887 awarded by the National Institutes of Health. The government has certain rights in the invention.

INCORPORATION BY REFERENCE OF SEQUENCE LISTING

The Sequence Listing, which is a part of the present disclosure, includes a computer readable form comprising nucleotide and amino acid sequences of the present invention submitted via EFS-Web. The subject matter of the Sequence Listing is incorporated herein by reference in its entirety.

INTRODUCTION

Astroviruses are non-enveloped, positive-sense, poly-adenylated RNA viruses often associated with gastrointestinal disease (De Benedictis, P., et al., Infect. Genet. Evol. 11: 1529-44, 2011; Mendez, E. and Arias, C. F., Fields Virology, $5^{th}$ ed. p. 981-99, 2007). To date, astroviruses have been isolated from a number of hosts, including wild and domestic animals, marine mammals, birds, and humans, and new astrovirus-susceptible hosts continue to be identified (De Benedictis, P., et al., Infect. Genet. Evol. 11: 1529-44, 2011; Finkbeiner, S. R., et al., Virol. J. 5: 117, 2008; Koci, M. D., et al., J. Virol. 74: 6173-7, 2000; Li. L, et al., J. Virol. 85: 9909-17, 2011; Phan, T. G., et al., PLoS. Pathog. 7: e1002218, 2011; Reuter, G., et al., Arch. Virol. 156: 125-8, 2011). The Human astroviruses (HAstV) in particular are an important cause of gastroenteritis in inpatient and outpatient pediatric, HIV-infected and immunocompromised, and elderly populations, and have been shown to cause sporadic outbreaks of gastroenteritis in immunocompetent adults as well (Belliot, G., et al., J. Med. Virol. 51:101-6, 1997; Coppo, P., et al., Ann. Hematol. 79:43-5, 2000; Cunliffe, N. A., et al., J. Med. Virol. 67: 563-6, 2002; Dennehy, P. H., et al., J. Infect. Dis. 184: 10-5, 2001; Finkbeiner, S. R., et al., J. Virol. 83: 10836-9, 2009; Gray, J. J., et al., J. Med. Virol. 23: 377-81, 1987; Grohmann, G. S., et al., N. Engl. J. Med. 329: 14-20, 1993; Herrmann, J. E., et al., N. Engl. J. Med. 324: 1757-60, 1991; Jeong, H. S., et al., Korean. J. Peds. 55: 77-82, 2012; Lewis, D. C., et al., J. Hosp. Infect. 14: 9-14, 1989; Mendez, E. and Arias, C. F., Fields Virology, $5^{th}$ ed. p. 981-99, 2007; Oishi, I., et al., J. Infect. Dis. 170: 439-43; Palombo, E. A. and Bishop, R. F., J. Clin. Microbiol. 34: 1750-3, 1996; Shastri, S., et al., J. Clin. Microbiol. 36: 2571-4, 1998; Wood, D. J., et al., J. Med. Virol. 24:435-44, 1988). As a viral agent of pediatric diarrhea, astrovirus is reportedly second only to rotavirus (Dennehy, P. H., et al., J. Infect. Dis. 184: 10-5, 2001; Mendez, E. and Arias, C. F., Fields Virology, $5^{th}$ ed. p. 981-99, 2007), with a seroprevalence of neutralizing antibodies to Human Astrovirus (HAstV) 1 nearing 90% by the age of 9 (Koopmans, M. P., et al., Clin. Diagn. Lab. Immun. 5: 33-7, 1998). Furthermore, given the incorporation of rotavirus vaccines into national immunization programs (Patel, M. M., et al., Lancet. Infect. Dis. 12: 561-70, 2012), the proportion of astrovirus-mediated diarrhea is likely to increase.

However, astrovirus disease is not limited only to the gastrointestinal tract. Astroviruses have been implicated as the cause of hepatitis in ducks and neurological disease in minks (Blomström, A. L., et al., J. Clin. Microbiol. 48: 4392-6, 2010; Gough, R. E., et al., Avian. Pathol. 14: 227-36, 1985). In humans, an astrovirus was identified as the cause of encephalitis in an immunocompromised child with X-linked agammaglobulinemia (Quan, P. L., et al., Emerg. Infect. Dis. 16: 918-25, 2010). Furthermore, we have previously reported the presence of the human astrovirus MLB2 in the plasma of a febrile child (Holtz, L. R., et al. Emerg. Infect. Dis. 17: 2050-2, 2011).

The Astroviridae family is divided into the mamastrovirus and avastrovirus genera—characterized by the ability to infect mammals and avian species, respectively. Across both genera, the astrovirus genome ranges from 6.1 to 7.7 kilobases (kB) in length, not including the 3'-polyadenylated tail, and contains three open reading frames (ORFs) and 5' and 3' untranslated regions (UTRs) (Mendez, E. and Arias, C. F., Fields Virology, $5^{th}$ ed. p. 981-99, 2007). ORF1a encodes a polypeptide of 920-935 amino acids (aa) in length containing conserved motifs, including a serine protease (De Benedictis, P., et al., Infect. Genet. Evol. 11: 1529-44, 2011; Mendez, E. and Arias, C. F., Fields Virology, $5^{th}$ ed. p. 981-99, 2007). A highly conserved heptanucleotide motif and downstream hairpin structure at the ORF1a/ORF1b junction generates a −1 frameshift (Jiang, B., et al., P. Natl. Acad. Sci. USA. 90: 10539-43, 1993; Lewis, T. L. and Matsui, S. M., Arch. Virol. 140: 1127-35, 1995) to lead to the translation of an ORF1a/1b polypeptide which is later cleaved into polypeptides corresponding to ORF1a and ORF1b (De Benedictis, P., et al., Infect. Genet. Evol. 11: 1529-44, 2011; Mendez, E. and Arias, C. F., Fields Virology, $5^{th}$ ed. p. 981-99, 2007). ORF1b encodes a polypeptide of approximately 515-528 as which contains the RNA-dependent RNA polymerase (Lewis, T. L., et al., J. Virol. 68: 77-83, 1994; Mendez, E. and Arias, C. F., Fields Virology, $5^{th}$ ed. p. 981-99, 2007). ORF2 encodes a 672-816 aa polypeptide which encodes the viral structural proteins including the capsid (De Benedictis, P., et al., Infect. Genet. Evol. 11: 1529-44, 2011; Lewis, T. L., et al., J. Virol. 68: 77-83, 1994; Mendez, E. and Arias, C. F., Fields Virology, $5^{th}$ ed. p. 981-99, 2007).

Despite the prevalence of astrovirus infection and the potential for extra-intestinal disease, there are no specific treatment protocols for astrovirus infection, and no vaccine exists. To date, little is known about the molecular mechanisms of astrovirus infection, replication, and disease pathogenesis, in part due to the lack of a genetically manipulable small animal model. Astroviruses have been identified as pathogens in humans as well as in a wide variety of non-human animals. Thus, it would be desirable to develop new approaches for treating or preventing diseases caused by astroviruses. This can be achieved by the development and testing of new vaccines and pharmaceutical agents using small animal models of astroviral diseases.

SUMMARY

The present inventors have utilized next generation sequencing (NGS) in combination with sequence analysis software (the pipeline VirusHunter software package) to identify a number of novel human astroviruses by analyzing the nucleic acid sequences generated by the Roche/454 next-generation sequencing platform (Voelkerding, K. V. et al., Clinical Chemistry 55: 641-658, 2009) or by Sanger sequencing (Sanger, F., et al., Proc. Nat'l. Acad. Sci. USA 74: 5463-5467, 1978) and their predicted translation products (Finkbeiner, S. R., et al., J. Virol. 83: 10836-9, 2009; Finkbeiner, S. R., et al., Virol. J. 5: 117, 2008; Finkbeiner, S. R., et al., J. Virol. 6:161, 2009). Whereas previous work in our lab identified murine norovirus as a common pathogen found in research mice, we applied our custom pipeline to further analyze the enteric virome of the research mouse (Karst, S. M., et al., Science. 299:1575-8, 2003; Thackray, L. B., et al., J. Virol. 81:10460-73, 2007; Wobus, C. E., et al., J. Virol. 80: 5104-12, 2006).

The present inventors have established that astrovirus can infect rodents such as, without limitation, laboratory mice. Accordingly, the present disclosure relates to methods of detecting astrovirus in mammals, in particular murine astrovirus in mice.

In various aspects, the present teachings can comprise methods of monitoring astrovirus infection in a population of mice, such as, in non-limiting example, in a colony of laboratory mice. The methods can comprise detecting a murine astrovirus antigen or nucleic acid in one or more animals housed in a colony.

In various embodiments of the present teachings, murine astroviruses can provide an animal model for developing and testing vaccines vaccination protocols, pharmaceutical agents, and therapeutic treatment protocols to prevent and/or treat diseases caused by astroviruses or linked to astrovirus infection. In various embodiments, the animal model can be a murine model. Because related astroviruses infect humans, a murine astrovirus model of infection can serve as a model system for developing vaccines and therapeutics that could be effective in preventing or treating human astrovirus-linked diseases, or astrovirus-linked diseases in non-human animals.

Thus, one embodiment can involve the use of mice that are infected with astroviruses. Any of a variety of strains of mice can be used. The present studies have shown that adaptive immunity is essential for restricting astrovirus replication as has also been shown to be the case in humans (Wood, D. J., et al., J. Med. Virol. 24:435-44, 1988). Thus, in certain embodiments, the murine model can include mice that are immunocompromised such as B-cell deficient mice (MuMT) or RAG deficient mice (RAG1$^{-/-}$).

In some aspects, the present teachings include selecting, monitoring, or modifying a treatment on the basis of the detection of the presence, absence or quantity of astrovirus in a subject. In these aspects, the detection of the presence, absence or quantity of astrovirus in a subject can comprise detection of astrovirus in a sample from the subject.

In some aspects, the present teachings include detection of a murine astrovirus using one or more nucleic acid probes. A probe of these aspects can comprise, consist essentially of, or consist of a sequence having at least 70% sequence identity with a sequence of a murine astrovirus nucleic acid, or a complement thereof. In various configurations, a sequence having at least 70% sequence identity with a sequence of a murine astrovirus nucleic acid, or a complement thereof, can have at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with a murine astrovirus nucleic acid, or a complement thereof. In various embodiments, a nucleic acid of the present teachings can be at least 10 nucleotides in length up to about 100 nucleotides in length.

In various embodiments, detection of a murine astrovirus can comprise a hybridization assay using a nucleic acid probe that hybridizes to a murine astroviral nucleic acid sequence under stringent conditions.

In various embodiments, detection of the astrovirus can involve the use of one or more nucleic acid probes including hybridization assays using a nucleic acid probe that hybridizes to a murine astroviral nucleic acid sequence under stringent conditions. Hybridization assays can include a southern blot, a northern blot, a dot blot, or a slot blot. In some aspects, murine astrovirus can be detected using a PCR assay such as an RT-PCR assay or a quantitative RT-PCR assay, or a sequencing-based assay such as a pyrosequencing assay.

In some embodiments, presence, absence, or quantity of astrovirus can be measured using an antibody probe that binds an astrovirus antigen to form an immune complex which can then be detected as to presence, absence or quantity of an immune complex.

In various embodiments, detecting a murine astrovirus in a subject can comprise a) providing a biological sample from the subject; b) contacting the sample with at least one antibody probe that binds at least one murine astrovirus antigen under conditions sufficient for formation of an immune complex comprising the at least one probe and the least one astrovirus antigen if present; and c) detecting presence, absence or quantity of an immune complex comprising the at least one probe and the at least one astrovirus antigen. In these embodiments, a sample can comprise astrovirus, or can be suspected of comprising astrovirus. An antibody probe can be a monoclonal or polyclonal antibody, or a portion thereof such as a Fab fragment. In some aspects, a murine astrovirus antigen can be a capsid protein or a portion thereof, or any other protein encoded by a murine astrovirus ORF, or a portion thereof. In some aspects, a murine astrovirus antigen can be immunologically cross-reactive with an astrovirus antigen hosted by another species. In various configurations, a murine astrovirus antigen of the present teachings can comprise, consist essentially of, or consist of at least 4, at least 5, at least 6, at least 7, at least 8, at least 9, at least 10, at least 11, at least 12, at least 13, at least 14 or at least 15 contiguous amino acid residues of an astrovirus polypeptide. In various configurations, a murine astrovirus antigen of the present teachings can comprise, consist essentially of, or consist of a full length, isolated murine astrovirus polypeptide, such as, in non-limiting example, an astrovirus antigen such as a capsid protein that is expressed in a microorganism such as an *E. coli* or yeast, or in a mammalian, avian, or insect cell culture. In various configurations, a murine astrovirus antigen of the present teachings can comprise, consist essentially of, or consist of a murine astrovirus antigen of less than full length, such as, without limitation, an astrovirus antigen consisting essentially of or consisting of up to 100 amino acid residues, up to 90 amino acid residues, up to 80 amino acid residues, up to 70 amino acid residues, up to 60 amino acid residues, up to 50 amino acid residues, up to 40 amino acid residues, up to 30 amino acid residues, up to 25 amino acid residues, up to 20 amino acid residues, up to 15 amino acid residues or up to 10 amino acid residues.

In various embodiments, detection of astrovirus in a sample can comprise, without limitation, determining presence, absence or quantity of an antibody against astrovirus in a subject. In some aspects, determining presence, absence or quantity of an antibody against astrovirus can comprise providing a sample from the subject; forming a mixture comprising a) the sample or antibodies comprised by the sample, and b) at least one astrovirus antigen, under conditions sufficient for formation of an antibody/antigen complex between the at least one astrovirus antigen and an anti-astrovirus antibody if present; and c) detecting presence, absence or quantity of an antibody/antigen complex.

In some aspects, methods disclosed in the present teachings comprise obtaining a sample from a subject, and detecting presence, absence or quantity of astrovirus in the sample. In various embodiments set forth herein, a sample from a subject can be a body fluid sample, such as, without limitation, a blood sample, a serum sample, a plasma sample, a cerebrospinal fluid sample, and/or a solid tissue sample. In some configurations, a blood sample can be a peripheral blood sample. In various configurations, a sample can comprise fibroblasts, endothelial cells, peripheral blood mononuclear cells, haematopoietic cells and various combinations thereof. In some embodiments, a sample can be a solid tissue sample, or a fecal (stool) sample. In some embodiments, a sample can comprise or can be suspected of comprising astrovirus.

In various aspects of these methods, detecting, diagnosing, monitoring or managing astrovirus in a subject can comprise providing a biological sample from the subject, and contacting the sample with at least one primary probe that binds at least one astrovirus antigen under conditions sufficient for formation of a probe/antigen complex between the at least one astrovirus antigen and the at least one probe, and detecting presence, absence or quantity of a complex comprising the at least one probe and the at least one astrovirus antigen. In some configurations, a probe that can bind a murine astrovirus antigen can be an antibody against a murine astrovirus antigen. In some embodiments, a primary probe can be any molecule that can bind a structure or antigen comprised by a murine astrovirus, such as an astrovirus protein or polypeptide, or an epitope thereof. In various configurations, the binding between a primary probe and a murine astrovirus structure or antigen can have a binding constant Kd of $10^{-5}$ or less, $10^{-6}$ or less, $10^{-7}$ or less, $10^{-8}$ or less, or $10^{-9}$ or less. In various embodiments, such primary probes can have high specificity, i.e., bind a murine astrovirus antigen with a binding constant less than that of a non-murine astrovirus antigen. Types of probes include, without limitation, an antibody, an antigen binding domain or antigen binding fragment of an antibody such as an Fab fragment, an aptamer (Jayasena, S. D., et al., Clinical Chemistry 45: 1628-1650, 1999), an avimer (Silverman, J., et al., Nature Biotechnology 23: 1556-1561, 2005) or any combination thereof. In various configurations, an antibody can be a monoclonal antibody, a polyclonal antibody or a combination thereof, and an aptamer can be an RNA aptamer, a DNA aptamer, a peptide aptamer, or a combination thereof. In various aspects, detection of binding of a probe to a polypeptide can comprise detecting a label bound directly or indirectly to the probe. A label can be any label known to skilled artisans, such as, for example, a radioisotope, a chromophore, a fluorophore, a quantum dot, an enzyme and a resonance light scattering (RLS) particle. In some configurations, an astrovirus antigen can comprise a contiguous sequence of at least 4 amino acids, at least 5 amino acids, at least 6 amino acids, at least 7 amino acids, at least 8 amino acids, at least 9 amino acids, or at least 10 amino acids of an astrovirus polypeptide.

In some embodiments, the present teachings include an antibody against an astrovirus such as a murine astrovirus, and methods of generating such antibodies. In various configurations, these methods include providing an astrovirus antigen such as a capsid antigen, inoculating a host animal such as, in non-limiting example, a mouse, a hamster, a rat, a rabbit, or a bird (e.g. a chicken or duck), and collecting body fluid such as, for example, blood, plasma, serum, from the animal to obtain a polyclonal antiserum (or egg yolk from a bird to obtain an IgY antibody, see Schade, R., et al., Altern. Lab Anim. 33: 129-154, 2005). Alternatively, a monoclonal antibody against an astrovirus antigen such as a capsid protein can be generated using established methods (see, e.g. Kohler G, Milstein C., Continuous cultures of fused cells secreting antibody of predefined specificity, Nature 256: 495-497, 1975; Schreiber, R. D., et al., J. Immunol. 134: 1609-1618, 1985; Harlow, E., Using Antibodies: A Laboratory Manual, Cold Spring Harbor Laboratory Press, Cold Spring Harbor, N.Y., 1999). In various embodiments, an astrovirus itself can be a source of antigen. Alternatively, an astrovirus antigen can be an astrovirus protein expressed by recombinant means. For example, an astrovirus capsid protein or a portion thereof encoded by a plasmid vector can be expressed in a prokaryote such as *E. coli*, and the recombinant polypeptide can serve as antigen for generating an antibody.

In some configurations of the present teachings, detection of binding between the at least one antibody and at least one astrovirus antigen can comprise any binding detection method known to skilled artisans, such as, without limitation, an immunoprecipitation, a radioimmunoassay, a Western blot, an ELISA or a flow cytometry (FACS) assay.

Various configurations of the present teachings include methods of detecting, diagnosing, monitoring or managing an astrovirus infection or astrovirus-related disease. In various aspects, these methods comprise contacting a sample or antigens thereof with at least one probe that binds at least one astrovirus antigen under conditions sufficient for formation of a complex comprising the at least one probe and the least one astrovirus antigen if present. In various configurations, the methods can comprise a) contacting a biological sample with a solid surface that binds at least one astrovirus antigen; and b) subsequent to a), contacting the surface with at least one probe. In some configurations of these aspects, the detecting presence, absence or quantity of a complex can comprise quantifying the at least one probe bound to the surface subsequent to b). In some configurations, the at least one probe can comprise a label, and the detecting presence, absence or quantity of a complex can comprise quantifying the label, which can be any label known to skilled artisans such as an enzyme, a radioisotope, a fluorogen, a fluorophore, a chromogen, or a chromophore.

In various embodiments, detection of binding between at least one probe directed against an astrovirus antigen, and an astrovirus or astrovirus antigen comprised by a sample can comprise direct detection, i.e., detection of a label comprised by the at least one probe, such as detection of a radioisotope or fluorophore comprised by the at least one antibody.

In various embodiments, detection of binding between at least one antibody directed against an astrovirus antigen (a "primary" antibody or probe), and an astrovirus or astrovirus antigen comprised by a sample can comprise indirect detection, comprising detection of a label comprised by a secondary probe such as a secondary antibody directed against the primary antibody, a labeled avidin, a labeled streptavidin, or a labeled anti-biotin antibody for detection of a primary probe that is tagged with a biotin, or a labeled anti-digoxygenin antibody for detection of a primary probe that is tagged with a digoxygenin.

In various configurations, an antibody or probe of these aspects can further comprise one or more labels, such as an enzyme, a radioisotope, a fluorogen, a fluorophore, a chromogen, or a chromophore.

A radioisotope of the various configurations can be any radioisotope known to skilled artisans, such as, for example, $^3$H, $^{14}$C, $^{32}$P, $^{33}$P, $^{35}$S, or $^{125}$I.

A fluorophore of the various configurations can be any fluorophore known to skilled artisans, for example a fluorescein, a rhodamine, a coumarin, an indocyanine, or a green fluorescent protein (GFP).

An enzyme of the various configurations can be any enzyme for which a suitable substrate is available, such as, for example, alkaline phosphatase, a horseradish peroxidase or a chloramphenicol acetyltransferase. A suitable substrate is a substrate that, when contacted by an enzyme, produces a product that is detectable by methods known to skilled artisans. For example, the substrate can be a chromogenic substrate, such as, for example, p-dinitrophenyl phosphate as a substrate for alkaline phosphatase, or diaminobenzidine as a substrate for horseradish peroxidase. An enzyme substrate can alternatively be, in various configurations, a fluorogenic substrate, such as, for example, disodium 4-methylumbelliferyl phosphate substrate for alkaline phosphatase, or a chemiluminescent substrate, such as, for example, 5-amino-2,3-dihydrophthalazine-1,4-dione (luminol) for horseradish peroxidase, or disodium 3-(4-methoxyspiro{1,2-dioxetane-3,2'-(5'-chloro)tricyclo[3.3.1.13,7]decan}-4-yl)phenyl phosphate for alkaline phosphatase.

A hapten of the present teachings can be any hapten for which a probe is available. For example, the hapten can be a biotin, detectable with an avidin, a streptavidin, or an anti-biotin antibody, or a digoxigenin detectable with an anti-digoxigenin antibody, by methods well known to skilled artisans.

In various configurations, a sample can be a biological sample obtained from a subject, such as a biological fluid sample or a biological tissue sample. A biological fluid sample can be, without limitation, a blood sample such as a sample comprising peripheral blood mononuclear cells (PBMCs), a plasma sample, a serum sample, a cerebrospinal fluid sample, a urine sample, or a saliva sample. A fluid sample can comprise cells, or can be cell-free. In some configurations, a fluid sample can be a peripheral blood sample. In some configurations, a sample can be a fecal (stool) sample.

In various configurations, a sample would be a cell culture sample, such as, for example, a culture supernatant from an astrovirus-infected culture, or a sample comprising cells from such a culture.

In various aspects of the methods, detecting astrovirus in a subject can comprise detecting presence, absence or quantity of antibodies against murine astrovirus in a sample from the subject, such as a fecal sample, a blood sample, a serum sample, a plasma sample, or a cerebrospinal fluid sample. These methods can include contacting a sample with a murine astrovirus or an astrovirus antigen such as, for example a polypeptide component of an astrovirus or a peptide comprising an epitope of a murine astrovirus polypeptide, and detecting formation of a binding complex comprising antibody comprised by the sample and the astrovirus or astrovirus antigen. In some embodiments, a murine astrovirus or astrovirus antigen can be immobilized on a solid support. In some configurations, a solid support can be, without limitation, an ELISA plate, a bead, a dip stick, a test strip or a microarray.

In some configurations, methods of the present teachings can comprise providing a solid surface to which one or more antigens comprised by a sample are bound, contacting at least one probe to the solid surface under conditions sufficient for formation of a complex comprising at least one probe and one or more astrovirus antigens, and detecting presence, absence, or quantity of a complex comprising the at least one probe and at least one astrovirus antigen. In various configurations, the detecting can comprise an ELISA, a radioimmunoassay, a Western blot assay or a flow cytometry assay. In some embodiments, presence, absence or quantity of a complex comprising at least one astrovirus antigen and at least one probe can be determined by immunoprecipitation.

In various embodiments of the present teachings, the inventors disclose methods of detecting, diagnosing, monitoring or managing astrovirus in a subject in a seroconversion-type assay. In various aspects, these methods can comprise providing a sample from the subject, and forming a mixture comprising the sample and at least one murine astrovirus antigen under conditions sufficient for formation of an antibody/antigen complex between the at least one murine astrovirus antigen and an antibody, and detecting presence, absence or quantity of an antibody/antigen complex, wherein the sample comprises circulating antibodies from the subject. In various configurations, a sample can be a body fluid sample, such as a sample comprising circulating antibodies. In various configurations, a sample can be a blood sample, a plasma sample, a serum sample, a cerebrospinal fluid sample, a fecal (stool) sample or a combination thereof. In various aspects, detecting the presence, absence or quantity of an antibody/antigen complex can comprise contacting the mixture with at least one probe directed against a circulating antibody under conditions sufficient for formation of a probe/antibody complex; and detecting presence, absence or quantity of the probe. In some configurations, the probe can be directed against murine immunoglobulin, and can be, for example, an antibody, an antigen-binding fragment thereof, an aptamer or an avimer. In some configurations, the probe can comprise a label. In some configurations, the at least one astrovirus can be immobilized on a solid support.

In various embodiments of the present teachings, the inventors disclose vaccines against astrovirus infection. In these embodiments, a vaccine can comprise, consist essentially of, or consist of a murine astrovirus antigen, or a portion thereof. In some embodiments, a vaccine can comprise a vector comprising a murine astrovirus nucleic acid that encodes an entire open reading frame of a murine astrovirus polypeptide, or a portion thereof. A vector can be, for example, an adeno-associated virus (AAV) such as, without limitation, an AAV5 vector.

In various embodiments of the present teachings, the inventors disclose methods of testing vaccines and anti-viral agents against astrovirus infection. In a typical protocol for a murine model, a vaccine or pharmaceutical agent would be administered to mice in a pre-treatment or treatment protocol, the mice would then be exposed to murine astrovirus through administration of the virus and/or through contact or co-housing with animals known to be infected with astrovirus. Outcomes of exposure would then be monitored.

In assessing a vaccine, the vaccine would be administered to infected mice and the effect of vaccination on the course of the infection monitored. Vaccine administration can be prior to administration of an astroviral challenge, at the about the same time or after administration of the astroviral challenge. The astroviral challenge can comprise, consist essentially of, or consist of administration of a preparation containing the astrovirus to one or more subject mice, exposure of a mouse or mice to an infected mouse or mice by co-housing or by any other suitable method that exposes an animal to the astrovirus.

A vaccine can comprise a murine astrovirus antigen, or a portion thereof. In some embodiments, the vaccine can comprise a vector comprising a murine astrovirus nucleic acid that encodes an entire open reading frame of a murine astrovirus polypeptide, or a portion thereof. A vector can be, for example, an adeno-associated virus such as, without limitation, an AAV5 vector.

In assessing a pharmaceutical agent, the agent can be administered after administration of the astroviral challenge. Any of a wide variety of agents can be tested in the model.

A candidate agent can be a candidate vaccine or a candidate pharmaceutical agent including synthetic, naturally occurring, or recombinantly produced molecules. Non-limiting examples include small molecules such as known anti-virals; drugs; peptides; antibodies (including antigen-binding antibody fragments, e.g., to provide for passive immunity) or other immunotherapeutic agents; endogenous factors present in eukaryotic or prokaryotic cells (e.g., polypeptides, plant extracts).

In various embodiments, candidate agents can encompass numerous chemical classes, though typically they are organic molecules, preferably small organic compounds having a molecular weight of more than 50 and less than about 2,500 Daltons. In some embodiments, candidate agents can comprise functional groups necessary for structural interaction with proteins, for example hydrogen bonding, and can include, for example, an amine, a carbonyl, a hydroxyl or a carboxyl group, preferably at least two functional chemical groups. In some configurations, a candidate agent can comprise cyclical carbon or heterocyclic structures and/or aromatic or polyaromatic structures substituted with one or more of the above functional groups. Candidate agents can also be found among biomolecules including, but not limited to: peptides, saccharides, fatty acids, steroids, purines, pyrimidines, derivatives thereof, structural analogs thereof or combinations thereof.

Candidate agents can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and can be used to produce combinatorial libraries. Known pharmacological agents can be subjected to directed or random chemical modifications, such as acylation, alkylation, esterification, amidification, etc. to produce structural analogs.

The outcome of infection can be monitored by any of a variety of methods including detection the presence, absence or quantity of astrovirus in a sample from an infected mouse, measuring immunochemistry aspects such as antibody produced in response to infection, detecting any symptomotology or any other suitable method.

The present teachings include, without limitation, the following aspects:

1. An isolated polynucleotide comprising, consisting essentially of, or consisting of a nucleotide sequence that is at least 70% identical to any one of SEQ ID NO:1, SEQ ID NO:2, SEQ ID NO:3, and SEQ ID NO:4, and wherein a virus comprising said polynucleotide is infectious towards a mammal.

2. An isolated polynucleotide in accordance with aspect 1, wherein the nucleotide sequence is at least 75% identical to any one of SEQ ID NO:1, SEQ ID NO:2, SEQ ID NO:3, and SEQ ID NO:4

3. An isolated polynucleotide in accordance with aspect 1, wherein the nucleotide sequence is at least 80% identical to any one of SEQ ID NO:1, SEQ ID NO:2, SEQ ID NO:3, and SEQ ID NO:4.

4. An isolated polynucleotide in accordance with aspect 1, wherein the nucleotide sequence is at least 85% identical to any one of SEQ ID NO:1, SEQ ID NO:2, SEQ ID NO:3, and SEQ ID NO:4.

5. An isolated polynucleotide in accordance with aspect 1, wherein the nucleotide sequence is at least 90% identical to any one of SEQ ID NO:1, SEQ ID NO:2, SEQ ID NO:3, and SEQ ID NO:4.

6. An isolated polynucleotide in accordance with aspect 1, wherein the nucleotide sequence is at least 95% identical to any one of SEQ ID NO:1, SEQ ID NO:2, SEQ ID NO:3, and SEQ ID NO:4.

7. An isolated polynucleotide in accordance with aspect 1, wherein the nucleotide sequence is 100% identical to any one of SEQ ID NO:1, SEQ ID NO:2, SEQ ID NO:3, and SEQ ID NO:4.

8. An isolated polynucleotide in accordance with aspect 1, wherein the mammal is a primate.

9. An isolated polynucleotide in accordance with aspect 1, wherein the primate is a human.

10. An isolated polynucleotide in accordance with aspect 1, wherein the mammal is a rodent.

11. An isolated polynucleotide in accordance with aspect 10, wherein the rodent is a mouse.

12. An oligonucleotide comprising, consisting essentially of, or consisting of a sequence consisting of about 10, from 10 to 70, or about 70 nucleotides, wherein said oligonucleotide hybridizes to a nucleic acid of a murine astrovirus or the complement thereof under high stringency conditions (Sambrook, J., et al., Molecular Cloning: A Laboratory Manual, 3rd ed. Cold Spring Harbor Laboratory Press, Cold Spring Harbor, N.Y., 2001; Ausubel, F. M., et al., ed., Current Protocols in Molecular Biology, Wiley Interscience, 2003).

13. An oligonucleotide in accordance with aspect 12, wherein the oligonucleotide comprises, consists essentially of, or consists of a sequence consisting of about 10, from 10 to 60, or about 60 nucleotides.

14. An oligonucleotide in accordance with aspect 12, wherein the oligonucleotide comprises, consists essentially of, or consists of a sequence consisting of about 10, from 10 to 50, or about 50 nucleotides.

15. An oligonucleotide in accordance with aspect 12, wherein the oligonucleotide comprises, consists essentially of, or consists of a sequence consisting of about 10, from 10 to 40, or about 40 nucleotides.

16. An oligonucleotide in accordance with aspect 12, wherein the oligonucleotide probe comprises, consists essentially of, or consists of a sequence consisting of about 10, from 10 to 30, or about 30 nucleotides.

17. An oligonucleotide in accordance with aspect 12, wherein the oligonucleotide probe comprises, consists essentially of, or consists of a sequence consisting of about 10, from 10 to 20, or about 20 nucleotides.

18. An oligonucleotide in accordance with aspect 12, wherein the oligonucleotide comprises, consists essentially of, or consists of a sequence consisting of about 15, from 15 to 60, or about 60 nucleotides.

19. An oligonucleotide in accordance with aspect 12, wherein the oligonucleotide comprises, consists essentially of, or consists of a sequence consisting of about 20, from 20 to 60, or about 60 nucleotides.

20. An oligonucleotide selected from the group consisting of

CCAAGAAAGAGGCACTAGTGGCACTC; (SEQ ID NO: 6)

GTTTTTTTTTTTTTTTTTTTGCCAATTTTTATGCCAATTATATCACC
C; (SEQ ID NO: 7)

TACATCGAGCGGGTGGTCGC; (SEQ ID NO: 8)

GTGTCACTAACGCGCACCTTTTCA; (SEQ ID NO: 9)
and

TTTGGCATGTGGGTTAA. (SEQ ID NO: 10)

21. A nucleic acid-based vaccine, comprising a vector comprising a murine astrovirus sequence encoding an astrovirus polypeptide or a portion thereof, wherein the vector is other than a murine astrovirus.

22. A method of detecting presence, absence or quantity of an murine astrovirus in a biological sample, the method comprising:
providing a sample comprising or suspected of comprising an astrovirus;
contacting the sample with at least one nucleic acid that is complementary to a nucleotide sequence that has at least 70% sequence identity with an astrovirus nucleic acid sequence, or the complement thereof, under hybridization conditions; and
detecting the presence, absence or quantity of a hybrid nucleic acid comprising the probe and the astrovirus nucleic acid.

23. A method of detecting presence, absence or quantity of an astrovirus in a biological sample in accordance with aspect 22, wherein the nucleotide sequence that has at least 70% sequence identity with an astrovirus nucleic acid sequence, or the complement thereof, has at least 75% sequence identity with an astrovirus nucleic acid sequence, or the complement thereof.

24. A method of detecting presence, absence or quantity of an astrovirus in a biological sample in accordance with aspect 22, wherein the nucleotide sequence that has at least 70% sequence identity with an astrovirus nucleic acid sequence, or the complement thereof, has at least 80% sequence identity with an astrovirus nucleic acid sequence, or the complement thereof.

25. A method of detecting presence, absence or quantity of an astrovirus in a biological sample in accordance with aspect 22, wherein the nucleotide sequence that has at least 70% sequence identity with an astrovirus nucleic acid sequence, or the complement thereof, has at least 85% sequence identity with an astrovirus nucleic acid sequence, or the complement thereof.

26. A method of detecting presence, absence or quantity of an astrovirus in a biological sample in accordance with aspect 22, wherein the nucleotide sequence that has at least 70% sequence identity with an astrovirus nucleic acid sequence, or the complement thereof, has at least 90% sequence identity with an astrovirus nucleic acid sequence, or the complement thereof.

27. A method of detecting presence, absence or quantity of an astrovirus in a biological sample in accordance with aspect 22, wherein the nucleotide sequence that has at least 70% sequence identity with an astrovirus nucleic acid sequence, or the complement thereof, has at least 95% sequence identity with an astrovirus nucleic acid sequence, or the complement thereof.

28. A method of detecting presence, absence or quantity of an astrovirus in a biological sample in accordance with aspect 22, wherein the nucleotide sequence that has at least 70% sequence identity with an astrovirus nucleic acid sequence, or the complement thereof, has 100% sequence identity with an astrovirus nucleic acid sequence, or the complement thereof.

29. A method of detecting presence, absence or quantity of an astrovirus in a biological sample in accordance with any one of aspects 22-28, wherein the detecting comprises a quantitative PCR assay.

30. A method of detecting presence, absence or quantity of an astrovirus in a biological sample in accordance with aspect 29, wherein the quantitative PCR assay is a quantitative RT-PCR assay.

31. A method of detecting presence, absence or quantity of an astrovirus in a biological sample in accordance with any one of aspects 22-28, wherein the detecting comprises a pyrosequencing assay.

32. A method of detecting presence, absence or quantity of an astrovirus in a biological sample in accordance with any one of aspects 22-28, wherein the detecting comprises a hybridization assay selected from the group consisting of a southern blot, a northern blot, a dot blot, and a slot blot, and a RACE assay.

33. A method according to any one of aspects 22-32, wherein the diagnostic sample is selected from the group consisting of a fecal sample, a vomitus sample, a tissue sample and a blood sample.

34. An isolated polypeptide comprising, consisting essentially of, or consisting an amino acid sequence at least 70% identical to at least 4 contiguous amino acids of a polypeptide encoded by an open reading frame comprised by a nucleotide sequence selected from the group consisting of SEQ ID NO:1, SEQ ID NO:2, SEQ ID NO:3, and SEQ ID NO:4.

35. An isolated polypeptide in accordance with aspect 34, wherein the nucleotide sequence is at least 75% identical to any one of SEQ ID NO:1, SEQ ID NO:2, SEQ ID NO:3, and SEQ ID NO:4

36. An isolated polypeptide in accordance with aspect 34, wherein the nucleotide sequence is at least 80% identical to any one of SEQ ID NO:1, SEQ ID NO:2, SEQ ID NO:3, and SEQ ID NO:4.

37. An isolated polypeptide in accordance with aspect 34, wherein the nucleotide sequence is at least 85% identical to any one of SEQ ID NO:1, SEQ ID NO:2, SEQ ID NO:3, and SEQ ID NO:4.

38. An isolated polypeptide in accordance with aspect 34, wherein the nucleotide sequence is at least 90% identical to any one of SEQ ID NO:1, SEQ ID NO:2, SEQ ID NO:3, and SEQ ID NO:4.

39. An isolated polypeptide in accordance with aspect 34, wherein the nucleotide sequence is at least 95% identical to any one of SEQ ID NO:1, SEQ ID NO:2, SEQ ID NO:3, and SEQ ID NO:4.

40. An isolated polypeptide in accordance with aspect 34, wherein the nucleotide sequence is 100% identical to any one of SEQ ID NO:1, SEQ ID NO:2, SEQ ID NO:3, and SEQ ID NO:4.
41. An isolated polypeptide in accordance with aspect 34, wherein the mammal is a primate.
42. An isolated polypeptide in accordance with aspect 41, wherein the primate is a human.
43. An isolated polypeptide in accordance with aspect 34, wherein the mammal is a rodent.
44. An isolated polypeptide in accordance with aspect 45, wherein the rodent is a mouse.
45. An oligopeptide comprising, consisting essentially of, or consisting of at least 4 up to 60, or about 60 amino acid residues of a murine astrovirus antigen.
46. An oligopeptide in accordance with aspect 45, wherein the oligopeptide comprises, consists essentially of, or consists of up to 50, or about 50 amino acid residues.
47. An oligopeptide in accordance with aspect 45, wherein the oligopeptide comprises, consists essentially of, or consists of up to 40, or about 40 amino acid residues.
48. An oligopeptide in accordance with aspect 45, wherein the oligopeptide comprises, consists essentially of, or consists of up to 30, or about 30 amino acid residues.
49. An oligopeptide in accordance with aspect 45, wherein the oligopeptide comprises, consists essentially of, or consists of up 20, or to about 20 amino acid residues.
50. An oligopeptide in accordance with aspect 45, wherein the oligopeptide comprises, consists essentially of, or consists of up to 15, or about 15 amino acid residues.
51. An oligopeptide in accordance with aspect 45, wherein the oligopeptide comprises, consists essentially of, or consists of up to 10, or about 10 amino acid residues.
52. An oligopeptide in accordance with any one of aspects 34-51, further comprising a label.
53. An oligopeptide in accordance with aspect 52, wherein the label is selected from the group consisting of a fluorphore, a hapten, an enzyme and a radioisotope.
54. An antibody directed against a polypeptide or oligopeptide of any one of aspects 34-51.
55. A method of detecting presence, absence or quantity of an astrovirus in a biological sample, comprising performing a virus detection assay selected from the group consisting of a cytopathic assay, an antibody assay and a protein detection assay.
56. A method according to aspect 55, wherein the cytopathic assay is selected from the group consisting of a dye exclusion assay, an enzyme release assay and an apoptosis assay.
57. A method according to aspect 55, wherein the antibody assay is selected from the group consisting of a Western blot assay, an ELISA assay, an immunofluorescence assay, an immunoprecipitation assay and a radioimmunoassay.
58. A seroconversion assay for detecting a murine astrovirus in a murine subject, comprising:
  providing a serum or plasma sample from a subject;
  contacting the sample with an oligopeptide of any one of aspects 45-53; and
  detecting presence, absence or quantity of a complex comprising the oligopeptide and antibody that binds the oligopeptide.
59. A method for screening a candidate agent for anti-viral activity against an astrovirus, the method comprising:
a) providing a mouse susceptible to a disease or condition caused by the astrovirus;
b) infecting the mouse with the astrovirus;
c) administering the candidate agent to the mammal; and
d) monitoring indices of infection wherein decreased indices of infection indicates anti-viral activity against the astrovirus.
60. A method according to aspect 59, wherein the astrovirus is MoAstV.
61. A method according to aspect 59, wherein the candidate agent is a vaccine.
62. A method according to aspect 59, wherein the candidate agent is pharmaceutical agent.
63. A method according to aspect 59, wherein the mouse is an immunocompromised mouse.
64. A method according to aspect 60, wherein the mouse is a MuMT or RAG1$^{-/-}$ mouse.
65. A method according to aspect 59, wherein the monitoring comprises detecting presence, absence or quantity of an astrovirus in a biological sample obtained from the mouse by performing a virus detection assay according to any one of aspects 22-33 or 55-57 wherein absence or decreased quantity of astrovirus indicates antiviral activity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Methods

Figure 1:
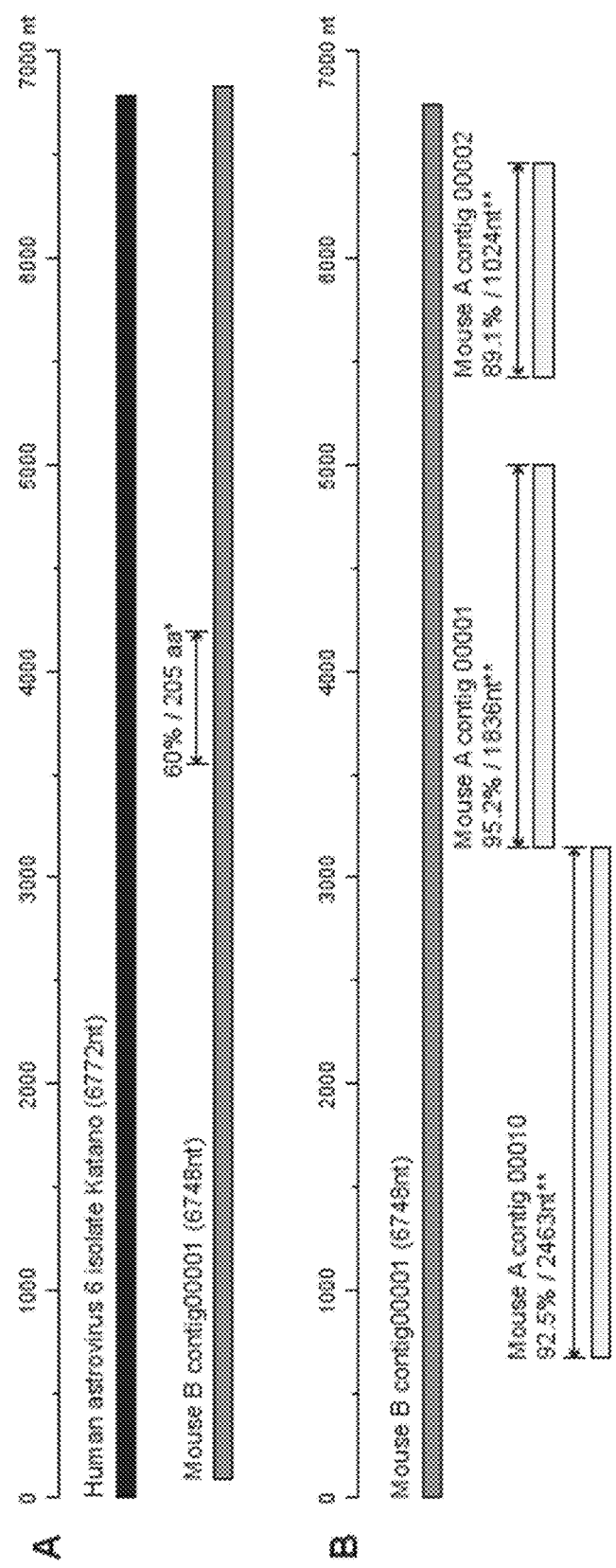
FIG. 1A-B illustrates a comparison between identified astrovirus sequences.

Methods and compositions described herein utilize laboratory techniques well known to skilled artisans. Such methods and compositions can be found described in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Harlow, E., Using Antibodies: A Laboratory Manual, Cold Spring Harbor Laboratory Press, Cold Spring Harbor, N.Y., 1999; Ausubel, F. M., et al., ed., Current Protocols in Molecular Biology, Wiley Interscience, 2003; Nagy, A., et al., Manipulating the Mouse Embryo: A Laboratory Manual (Third Edition), Cold Spring Harbor Laboratory Press, Cold Spring Harbor, N.Y., 2003. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. These publications are incorporated herein by reference, each in its entirety.

As used herein, the singular forms "a", "an" and "the" are intended to include the plural forms as well, unless the context indicates otherwise. Examples presented herein are illustrative and are not intended to be limiting to the scope of any claim.

Sequences of murine astroviruses of the present teachings include the following:

```
>Mouse_Astrovirus_STL_CY1_20120531_Update
                                                       (SEQ ID NO: 1)
CCAAGAAAGAGGCACUAGUGGCACUCCUGCUGCUAGUAAGUCUGACAUGGCCCUG

CGUAAGGAGUAUACUUCCCUUGUGGACCAAGCGGUCGACGCUGGGAAUUACCUG

GCCCGCUGCCAGUUGCCAACUACGGCAAUUCUGCUGCUGCGCAAUAUGCCUGACC

ACUAUCCUAACCGGCCUUGGUCUGUCCAUUCGACCCCCCGCCAUUUGGUCUAUCC

CUCAACAACGGAUGAUCCAAAGACGCGGGUUAUAACAGCCUCCUCCGUCACAGUG

GAGGAUGAAUGGGUGACCUAUGUCUGGACCGGCGCGCUGGCAGCAGGUGGCA

ACGGCCCCUGACUGUGGAAAAACGAUCCUGGUCUGUGCCCUCCUGAACGAACAUA

AGCGGCUCAAGGAUGAGAAUGCAAGCCUUAAACUUGCCAAGGCGAAUUUGGAGG

UUGAUAACACCACACUGCGGGUGGCGUCAGCGGCCAUUACCAACUCGGCCCCUCG

CCGUUCGCGCCUCCCUUGGAUCCUGGCACUCUUGGCUGUGCUUUUCUCCCUCCUC

ACGACCUCGGCUGCCUUUGAAACCAGCUCUACCUCACGGAGCUAUGCCCCUGAGG

AUAUUGCUAGGCACUCUGAGGAUUUGAACACCUUUAUUGAGAACGCUUUGAGGG

UGAACCACACACGCUCCUACACAGAGUACACCUACCAACUGUACGCCACACAUGC

UCAGACUUUCUUGGACCGCAUGGCCUUGACAUUUAACACCUGGCAAGCUUAUGAU

CCGCACUUCUUUGCGAAAACACCCUUGCAAAGUGCGCUUCUGAGUGUCCUCCAGU

AUGUAACACCCUGGACGUGGGAGAUAGCCCUUACGGGCUUGGUAUUGGCGCUCA

UGCUAGCGGAAAACUCUAGCCCUUGGUCGCUGCUCUACCUGGCCUGUGCUACUCU

CACAAGGACCCGCUUUGCCCUCUUGGCCGUGGCGCCCUUCCAGACACGCUACACG

ACGGCUGUCACCGUUGCCGCCUCGGUGCUCUACGCACUCGACCCCUUGGUCGCAG

UGGCGUGCCUGGUGCUACACCUCUUUCUCCUGGCAGUGGUGGGGCUCUUCAUGGA

GGAUACCUCCUAUGUCCAAAACUUGAAGGGCGCCUUCCUGCUGCUAUGCGCCUUC

UUCGGCCAUGCCCUCUGUGCCUCUUCGGAGUGAGCUCGGCGCCAGUCACAACAC

UAGCUGUUGCCUGGCGGAUCUGGCGGCUACUCUCUCGUGCCGGAACAACAGGCAC

CGUGGAGGUGCGCAAUGAAGAAGGCAAGGUGGUCUCAAAACAGACCACGCAACCC

AACUUCCUCUUCCGCUUCAAGCAGGCGUUGAGGAGGAUGAGACAACUCAGAACGA

CCCAGACCCCCUAGCGCGCGUCAAUCCUGAUGCGCUCUGCCACAUCAGCGUGGC

CGGGGCGAAAGGCACUGGCUUCUUUUGUGGUAACUACGCUGUGACAUGUGCACA

CGUAGUCGGGAGUGAGACAGUCGUCAACCUGUGCUAUAAAGGCCGUAACUAUCA

GGCCCCAGUGAAGAAAAUCCUGGAGCAAAAGGAUGUGGCACUCAUUCCCAUACCU

GCGGGGAUAACACCACCCCGCUUGAAGAUCUCCAAGAAGCACUGCUGCGACUGGG

UCUGUGUCUGUGCCCCCGACGGUGAUGGUGCCUACCUAACUGCUGUGACUGAGGG

UUGCGAGCAUGAUGGUCACUACUCCUAUGCCUGCCCGACGCGGGAUGGGAUGUCU

GGCGCUCCUCUGUUAGACAUAGAUGGCCAUGUUCUUGGGAUACACACUAACAACA
```

-continued

CUGGCUACACUGGUGGUGCCCAACGCCUCGACCUUGAGGACAUAGUUGAAGCCCC

CAAGCCAAAUCCCAAGCAGCUCGCCCUCGAGAGGGAGAUUGAAGAACUGAAAAAG

CAGCUUGCGGCCCUGCAGCCUGAACCACCUAGGCCUGAGCCCGUGGCUGCCCCUC

CCUCACCCGUUCAGCCCGGCCCCCUAGUGGUUCCAACUACCUGCCCCCCUCCAGCC

CCACCGGCACCAACUGUGGCCCCUGCUCCUGUGGCCCCCAGCCCUGUGGCGCACU

AUGUGGUCAAACCCACCCAAAUUCCACCUAUGCAACAAAGCCUAACAACUAGUGA

UGUGGUGGAUCUUGUGCGUGCGGCAAUGGGUCGUGAGAUGCAAAUCCUGCGGGA

CGAGCUGAACCUGAUGAAUCAGGCUAAAGGGAAGACCAAACGUGGCCGUGGGAA

GAAGCAUACCAUCGGGGCUCGUGUUGGUGGCCGUCGCAGACAGCGUGGGCCUGCC

UUCACCGAGGAGGAGUACAAGGAGAUGCUGGACCAAGGGAUUGACCCCGAUGAG

AUCAAGCGCCUAGCCGAAGACCUCGGGGAGGACCAGACUGGCUUCCCGGAGUGGA

GUGACCCUGAGUUCUCUGAUGAGGACGAUGGUUGGACACCAAAGACCCAUGACU

GGCUAGACUUUGAUUAUGAGGAUGAUUUGGAACAAACUUACGUCCCIUGGUCCCU

GGGCCCAGAAAUGCAAGAUACCUCUCGUCGACUACGUCAAGAAGAUCUUUGACAA

AGGCUCCGUUGAUGAGAUGUUACAAAAUCUUGCCCCUCUGGAGAAGAAGCUCUG

UAGGAAACAACUUGAGGCCGUUCGCCAGGCAAAAACUGAUAUCGAGCUCUCUGU

UGCACUUGGCGCUUUGGAUCGUCGUGCUGCCGAUGUGGGCAUGCAGCCCUUUACA

CCAGGGCUAGAGUAUAAACAAGCUGUUCCAAAAAACGCCAAGGGCCCCCGCAAGG

GGGCAAAAGAUCAGGGCUCGAAGACUGGAAAGAACUAAGGCAGCCCCCCUUUCGC

CUCCUGGUACCCCAGCCUUACCCUGUUGUCUGCAGCUUACCCCUGGACCGGCCCA

UCUAUGACAACGAUGAGCCUAAAGAUCCACUUCUGGGGGUGUUGCCACAUGUAG

ACUAUGAGGGUAACUUUGCACCAACAACCUGGGGAGGCGCAGCUUACGCGAAGA

GUUUCGAGAAGUUCACGUAUGCUCAACCUGUGGACUUCGAAAAGCACUAUCCUG

UAGAAACUCAGUUCGCUGACUGGGCCUGGCGAGUCCACCACGCUUACCUGGAAGG

CACUCGGGUAUGCCACAUCAUGUCUACAGAGAAAAAUACCGACUCAACCCCUGCC

UACCCCAAAUGCCUGGACUACUCCACCGAGGCCGACUACCUAGAGGAACAUGGCU

GGGAGCCCUAUGUCAACGCUUUCCGUGCCAUUGACUCCGGGGAGCGGCCCCAGGU

UCUCUGGUUCCUCUUCUUGAAGAAGGAGAUUCUCAAACAAGAGAAGAUUCGCGA

UUCAGACAUUCGUCAGAUUGUCUGUUCAGAUCCCAUCUAUGCGCGGAUCGGAGCU

UGCUUCGAACAACAUCAAAACCAUCUCAUGAAGCAAAAAACAGAGACCCAUUCCG

GGCAAUGUGGCUGGUGCCCCCUGAAGGGGGGCUUUGAGGCAAUGUGCCACCGUCU

UGCCUCUAAGCAGGGUGUCUUUGUGGAAUUUGACUGGACACGCUUUGAUGGAAC

AAUCCCCGUACAACUCUUCCGCAGGAUAAAGAAGCUCCGCUGGUCCAUGAUUUGU

CCCGAACAUCAGCAGCGCUACGGGCACAUGUACCAGUGGUAUGUUAACAAUCUCU

UGCACCGCUACACCGUGCUGCCCUCAGGUGAGGUGACCAUCCAAACUCGUGGCAA

CCCCUCAGGGCAAAUCUCAACAACAAUGGAUAACAACAUGGUUAACUACUGGCUU

CAGGCAUUUGAGUUCUGCUACUUCUUUGGCCCUGAUAAAGAUCUCUGGCGGCAG

UAUGAUACUGUCUGCUAUGGUGAUGACCGGCUUACGCGCUACCCUGUGCUACCAC

CCCAUUACAUCGAGCGGGUGGUCGCCAUGUACAAGGACAUCUUUGGCAUGUGGG

UUAAACCUGAAAAGGUGCGCGUUAGUGACACCCUGGUUGGUCUCACCUUUUGUG

GCUUUAGAAUAGGGGAGCACUAUUUGCCCUAUCCUGCACAGGAAGACAAACUCU

-continued

UUGCCGGCCUCGUCCGGCCAGUGAGGAAAUUGGCUGACUUUAAAACACUCCAUGG

GAAACUCUUGAGCCUGCAGCUUCUGAUGCACUUCCACCCUCCGAGUCCCUUUAAG

GACUACUUGGAGAUGUGCUUGGCAAACACCGCCAAGUACUGCCCGGAACUUCCGG

CGCGGUUUUCAGAGCGUCAGAUGGACAAGCUUUGGAGGGGAGGACCAAAAGCUG

UUCAUGGCUAAGGCCAAACAACAACAGAAAAAUGCCACGACCGUCACUACUACAA

CUGUCACUGGUCGCAGUAGUCGGCGGUCUCGCAGGCGCUCUGUACGGCGCCGCGC

UGCAGGCCCUUCUAACCCCCCAACAAAGACAACAACUGUUCGGACUGUUUUUCGC

CGCACUGCCCGGCCUCGCGGUGAUCGCCGCAGGAGUAGGAAUGCUCAGCGGCAGG

CUCCUCGCGAGGUUGUUCAGACGGUUACGGCGACCCUCGGAACGGUUGGCGCGAA

CCAGGGCAAUCAGGUCGAGCUUGAGAUGGCAGCGCUCCUCAACCCAGCGCUAAUU

AAAGAAACAACUGGCUCAAACGCCUUCGGACCACUCCAGAUGUAUGCCUCCACGC

AUGCCAUGUGGAAAGUGGAUAGGCUCACACUCAAGCUCACCCCUCUGGUCGGCGC

CUCUGCUGUUUCCGGUACAGCGGUCCGUGCCUCACUGAAUAUGACAUCUGGGCCC

GCCGCGCCCGCCUGGUCAGCCUUGGGCGCGCGGAAGCAUGUGGACACCAAUCCUG

GUCGGCCGGCUUCCUUCACCCUCACAGCCGCCGAUGUACCUGGCCCCAAGCAGGG

UUGGUUCUUUACUAAUACUAAGCAGGAGGCCGGCUUUACAGUCGGCGGGGCCAU

UGAGAUCCAUACCCUCGGCAAGACGAUGUCAACCUACCAGAACUCAGCCUAUACG

GGCCCACUCUUUCUUGCCGAGGUCACAGGUACCUGGAGGUUUAAGAACUACGAGC

CCCAGCCCGGCUUGCUCAACCUCCUCAAGACCGAGGUUAAAGAGCCUGCGGGCAC

UGUGAAGGUACACUCCAAACCUGGAGAACCUGUCACGCUCUCCAUCCCUCAAGCA

GGGACCUUUGCUGGCCUAGAGAGGCUAAAUCCAACAGCCUCGGCCACACCAGGUG

AGAUCAUCGGGGAGGUAGUGGAUUCCGCUGCGAAUGCGGUCUCCGGCUUGCUUCC

UCAACCCUGGCAGUGGCUUUUUAAAGGCGGCUGGUUCUUCCUGAAAAGAAUUGC

CAACCGGAAACCUGUUGGUGCCGCCAGUGUGGCGGGUGAACCUGAUGGAGGUGA

AGUGACUUUCCGCGUGUACGCCAGUAUCGCGGAUGCCCAGAAUGAUGUGCCCUGU

AUUGCCAGCUCGGCGGCCUCCACUCAAUCCAUACAGACGGAGGGUCUCAAGAUCU

CCCAGGUGACUCCUGGGACCAUUGGUAUGCCUGAAACUGCAGUAGCCACACACAA

CAUGGCUCCACCACCCGAGUCCGGACCCUAUACCUAUCAAGGGCCCACCUUGGAG

GCUGCUGCUCCUUUGCACGCCCCAAGUAUACACAGUGGACUAUUGUAGAUGCUG

GUACCUCCCAGGAGCAGGCCCGCCUGCGCUCCGGGGUGGUCCCAGCAGAGCAGAC

CUCAGCCUGGUCGAGCUGUACUCUGGAGCUCCCAGGCACCUUCCUCCAGAAUAUG

UAUGAGAUUGAUCCCCGUGAUAUUGCAGCCGGUACCUUUCCCAUCAAUCACUGGA

ACGUGAGCACCUCGCGGCUCACGCGGCUUGGCACCGCCUACGGUUGCAAUCAGGC

GCGGGUCCGCACCUAUGGGGAGGGAGUCCCGCAUGUGGUUAUCUCUACCACUUCU

GUCCUCUGGAUGGCCGACGUUUCCACAGGGUGGAACUAUGACAACUUCUCCGCUG

CCAUCUGGAAUCCCAUAGUGGUAGCUGGGCCAAACGUCCAUGGGACUGAACAGGG

CAUUCCUCUCACCCGGGGAACCCUCAACUGGCCCGGGGGCGAUAGGAAUCGCUGG

CCCUACCGCAACCAGAUUGAGAAGGGUCACUGGUAUGUGACCUUCUGGACUCAGU

ACGAUCCUGAUGAGUGGGUCUGGUUGGAUGAGUUCCAUCUCCAGUUCACCUUGC

AACCGGGCACGCACACCCCCACUGAAAACCAUUACUGGGAUGUAACAGCAGACAG

-continued

CUUAGGUACUGGCCUCUGGGGCCUCCGGGACCUUGUGUUCUACCCAAUAGGUACC

CAGCCCAGGAUAGUGAUACCAAACACUGGGCCUACCAGCUCCCAUGUGACCUUCG

ACCUCCCCCGGGUGAGGGCGAAGAUUACUCUACAGAUGAGGAAGGCGAGUCCGA

UGAGGGAGCUGAGGAUGAUGAAGGAAAUCCCCUUGAAUUUGACCACCCAUUAGA

CGGCGAUCUCUCGCAACCCCCCGCCGCCGUCCUGAAAGAUCUGACCUACAAGGGG

CGUAAUCUCGCCAAUGAAUUGUGGAGUACGGGGGUGCCAGAUGCGAAGGCCUGG

CUGGCGGGACAGACCAUCGACCCGUCGCCAUCCUUUCGCCGCUGGCGAGAGACUU

UUCAAAAAGCGCUCCAGCGUGGUGUAGCACCCCUGGAAGCGCAUGAGCUCGCUAC

UAGCGAGUUCCUUGCUCAAAGAGAAAGCCGCGGCCACGCCGAGUAGGAUCGAGGG

UACAGCUUUCUCCCCUGCUUUUCUGCUUCUUUCUGUGCUUUGGUGUUACUUUAGG

GUGAUAUAAUUGGCAUAAAAUUGGCAAAAAAAAAAAAAAAAAAA

>Mouse_Astrovirus_STL_CY2_20120531_Update
(SEQ ID NO: 2)
CCAAGAAAGAGGCACUAGUGGCACUCCUGCUGCUAGUAAGUCUGACAUGGCCCUG

CGUAAGGAGUAUACUUCCCUUGUGGACCAAGCGUUCGACGCCGGGAACUAUCUGG

CCCGCUGCCAGUUGCCAACUACGGCAAUUCUGCUGUUGCGCAACAUGCCCGACCA

CCACUCCAAUCGGCCCUGGUCUGUCCAUUCAACUCCCCGCCACUUGGUCUAUCCC

UCAACAACGGACGACCCAAGGAUGCGGGUUAUAACAGCCUCCUCCGUAACAGUGG

AGGAUGAAUGGGUGACCUAUGCCUGGACCGGUGCGCGCUGGCAGCAGGUGGCAA

CGGCCCCUGAUUGCGGGAAGACGAUCCUGGUCUGCGCCCUCCUGAACGAACAUAA

GCGGCUCAAGGAUGAGAAUGCAAGCCUCAAACUUGCCAAGGCGAACUUGGAGGU

UGAUAACACCACACUACGGGUGGCGUCGGCGGCCAUCACCAACCCGGCCCCUCGC

CGCUCGCGCCUCCCCUGGAUCCUGGCACUCUUGGCUGUCUUCUUCUCCCUCCUCA

CGACCUCGGCUGCCUUUGAAACCAGCUCUACCUCGCGGAGUUAUGCCCCUGAGGA

UAUUGCUAGGCACUCUGAGGACUUGAACACCUUUAUUGAGAACGCUUUGAGGGU

AAACCAUACACGCUCCUACACGGAGUACACCUACCAACUGUAUUCCACACAUGCU

CAGACUUUCUUAGAUCGCAUGGCCUUGACAUUCAACACCUGGCAAGCCUAUGAUC

CGCACUUCUUUGUGAAAACACCUCUGCAAAGUGCGCUUCUGAGUGUCCUCCAGUA

UGUAACACCCUGGACGUGGGAGAUAGCCCUUACGGGCUUGGUGCUGGCGCUCAUG

CUAGCAGAGAAUACUAGCCCUGGGCGCUGCUCUACCUAGCCUGCGCUACUCUCA

CAAGGACCCGCUUUGCCCUCUUGGCCGUGGCGCCCUUCCAGACACGCUACACGAC

GGCUGUAACUAUUGCCGUCUCGGUGCUCUACGCACUCGACCCCUUGGUCGCUGUG

GCGUGCCUGGUGCUACACCUCUUUCUCUUGGCAGUGGUGGGGCUCUUCAUGGAGG

ACACCUCCUAUGUCCAAAACUUGAAGGGCGCCUUUUCUGCUGCUAUGCGCCUUCUU

UGGCCACGCCCUCUGCGCCCUCUUCGGAGUGAGCUCGGCGCCAGUCACGACACUG

GCUGUCGUCUGGCGAAUCUGGCGGCUACUCUCUCGUGCCGGAACAACAGGCACUG

UGGAGGUGCGCAAUGAAGAAGGCAAGGUGGUCUCAAAACAGACCACACAACCCA

ACUUCCUCUUCCGCUUCAAGCAGGCGUUGAGGAGGAUGAGACAACUUAGAACGAC

CCAGACCCCCCUGGCACGCGUCAAUCCUGAUGCGCUCUGCCACGUCAGCGUAACC

GGGGCGAAGGGCACUGGCUUCUUCUGUGGUAACUAUGCUGUGACAUGCGCACAC

GUAGUUGGGAGUGAGACAGUUGUCAACCUGUGCUAUAAAGGCCAUAACUACCAG

GCCCCAGUGAAGAAAAUCCUGGCGCAUAAGGAUGUGGCACUCAUUUCCAUACCAA

-continued

```
CGGGGCUAACACCACCCCGCUUGAAGAUCUCUAGGAAGCACUGCUGCGACUGGGU

CUGCGUUUGUGCCCCCGACGGUGAUGGCGCCUACCUAACCGCUGUAACUGAGGGU

UGCGAGCAUGAUGGUCACUACUCCUACGUCUGCCCGACGCGGGAUGGGAUGUCUG

GUGCUCCUCUGCUAGACAUAGAUGGCCAUGUCCUUGGGAUACAUACCAACAAUAC

UGGCUAUACUGGUGGUGCCCAACGCCUCGACCUUGAUGAUAUAGUUGAGCCCCCC

AAGCCAAGUCCCAGGCAGCUCGCCCUCGAGGCGGAGGUUGAAAACCUGAGAAAAC

AGCUCGAAAGUCUGCGGUCUGAACCCUUUAGGCCUGAGUCCGUGGCUGCCCUCUC

UUCAACCGUGCAGCCCGGCCCCCUAGUGGUUCCAACUACCUGCCCUCCUCCAGCCC

CACCGGCACCAACUGUGGUCCCUGUUCCCGUGGCCCCUAGCCCUGUGGUUAAACC

CACCCAAACUCCACCUAUGCAACAAAGCUUGACAACUAGUGAUGUGGUGGAUCUU

GUGCGCGCGGCAAUGGGUCGUGAGAUGCAAAUCCUGCGGGACGAGUUGAACCUG

AUGAAUCAGGCUAAAGGGAAGACUAAGCGUGGCCGUGGGAAGAAGCACACUAUC

GGGGCUCGUGUUGGUGGCCGCCGCAAACAGCGUGGGCCUGCCUUCACUGAAGAGG

AGUAUAAGGAGAUGCUGGACCAAGGGAUUGAUCCCGAUGAGAUCAAGCGUCUAG

CUGAAGACCUCUGGGAGGACCAGACUGGUUUCCCAGAGUGGAGUGAUCCUGAGU

UCUCUGAUGAGGACGAUGGCUGGACACCAAAAACUCAUGAUUGGCUAGACUUUG

AUUAUGAGGAUGACUUGGAACAAACCCAUGUCCCUGGUCCCUGGGCCCAGAAAUG

CAAGAUACCUCUCGUCGACUAUGUCAAGAAGAUCUUUGACAGAGGCUCUGUUGA

UGAGAUGUUACAAAAUCUUGCCCCCCUGGAGAAGAAGCUCUGUAGGAAACAGCU

CGAGGCCGUCCGCCAGGCAAACACUGAUAUCGAGCUUUCCGUUGCACUUGGCGCC

UUGGAUCGUCGUGCUGCCGAUGUCGGCAUGCAGCCCUUUACACCAGGCCUAGAGU

ACAAACAGGCUGUUCCAAAAAACGCCAAGGGCCCCCGCAAGGGGGCAAAAGAUCA

GGGCUCGAAGACUGGAAAGAACUGAGGCAGCCCCCCUUUCGCCUCCUGGUACCCC

AGCCUUACCCUGUUGUCUGCAGCUUACCCCUGGACCGGCCCAUCUAUGACAACGA

UGAGCCCAAAGAUCCGCUUCUGGGGGUGUUGCCACAUGUGGACUACGAGGGUAA

UUUUGCACCAACAACCUGGGGAGGCGCAGCCUACGCGAAGAGUUUCGAGAAGUUC

ACAUACGCUCAACCUGUGGACUUCGAAAAGCACUAUCCUGUAGAAACUCAGUUCG

CUGACUGGGCCUGGCGAGUCCAUCACGCCUAUCUGGAAGGCACUCGGGUCUGUCA

CAUCAUGUCUACAGAGAAAAAUACCGACUCGACCCCCGCCUACCCCAAAUGCCUG

GACUACUCCACCGAGGCCGACUACCUGGAGGAACAUGGCUGGGAGCCCUAUGUCA

ACGCCUUCCGUGCCAUCGAUUCCGGGGAGCGGCCCCAGGUUCUCUGGUUCCUCUU

CUUGAAGAAGGAGAUUCUCAAACAAGAGAAGAUUCGCGACUCAGACAUUCGUCA

GAUUGUCUGCUCAGAUCCCAUCUAUGCGCGGAUCGGAGCUUGCUUCGAACAACAU

CAAAAUCAUCUCAUGAAGCAAAAAACAGAGACCCACUCCGGGCAAUGUGGGUGG

UGCCCCCUGAAGGGGGGCUUUGAGGCAAUGUGCCAUCGUCUUGCCUCUAAGCAGG

GUGUCUUUGUGGAAUUUGACUGGACACGCUUUGAUGGAACAAUCCCUGUACAAC

UCUUCCGCAGGAUAAAGAAGCUUCGCUGGUCCAUGGUUUGCCCCGAACAUCAGCA

GCGCUACGGGCACAUGUACCGGUGGUAUGUUAACAACCUCCUGCACCGCUACACC

GUGCUGCCCUCAGGCGAGGUGACCAUCCAAACUCUGGCAACCCCUCAGGGCAAA

UCUCAACAACAAUGGAUAAUAAUAUGGUUAACUACUGGCUUCAGGCAUUUGAGU
```

-continued
UCUGCUACUUCUUUGGCCCCAAUAAGGAUCUCUGGCGGCAGUAUGAUACUGUCUG

CUAUGGUGAUGACCGGCUCACGCGCUACCCUGUGCUACCGCCCCACUACAUCGAG

CGGGUGGUCGCCAUGUAUAAGGACAUCUUUGGCAUGUGGGUUAAACCUGAAAAG

GUGCGCGUUAGUGACACUCUGGUUGGUCUCACCUUCUGUGGCUUUAGAAUAGGG

GAGCACUAUUUGCCUUAUCCUGCACAGGAAGAUAAACUCUUUGCCGGCCUCGUCC

GGCCAGUGAGGAAAUUGGCUGACUUCAAAACACUCCAUGGGAAACUCUUGAGCC

UGCAGCUUCUGAUGCACUUUCAUCCUCCGAGUCCCUUCAAGGACUACUUGGAGAU

GUGCCUGGCAAACACCGCCAAGUACUGCCCGGAACUUCCGGCGCGGUUUUCAGAG

CGUCAGAUGGACAAGCUUUGGAGGGGAGGACCAAAAGCUGUUCAUGGCUAAGGC

CAAACAACCACAGAAAAAUGCCACGACCGUCACUACUACAACUGUCUCUGGUGGC

AGUAGUCGGCGGUCUCGCAGGCGCUCUGUACGGCGCCGCGCUACAGGCUCUUCUA

ACCCCCCAACAAAGACAACAACUGUUCGGACUGUUUUUCGCCGCAAUACCCGGCC

UCGCGGUAAUCGCCGCAGGAGUAGGAAUGCUCAGCGGCAGGCUCCUCGCGAGGUU

GUCCAGACGGUUACGGCGACCCUCGGAACGGUUGGCGCGAACCAGGGCGAUCAGG

UCGAGCUUGAGAUGGCAGCGCUCCUCAGCCCAGCGCUGAUUAAGGAAACAACUGG

UUCAAACGCCUUUGGGCCACUCCAGAUGUAUGCCUCACGCAUGCCAUGUGGAGA

GUGGACAGGCUCACACUCAGGCUCACCCCCUGGUCGGCGCCUCUGCCGUUUCCG

GCACAGCAGUCCGUGCCUCACUGAACAUGACAUCUGGGCCCGCUGCGCCCGCCUG

GUCAGCCUUGGGCGCGGAAGCAUGUGGAUACCAACCCUGGUCGGCCGGCUUCC

UUCACCCUUACAGCCGCCGAUGUACCUGGCCCCAAGCAGGGCUGGUUCCUUACUA

ACACUAAGCAGGAUGCCGGCUUUUCAGUCGGCGGGGCCAUUGAGAUACACACCCU

CGGCAAGACGAUGUCAACUUAUCAGAAUAAAGCCUAUGAUGGCCCACUUUUUCU

UGCCGAGGUCACGGGCACCUGGAGGUUUAAGAACUAUGAGCCCCAGCCCGGCAUG

CUCAACCUCCUCAAGACCGAGGUCAAGGAGCCCGCGGGUACUGUGAAGAUCCACU

CCAAGCCUGGAGAACCUGUCACGCUCUCCAUCCCUGAAGCAGGGACCUUUGCUGG

CCUAGAGAGGCUAAAUCCAACAGCCUCGGCCACGCCAGGUGAGAUCAUCUGGGAG

GUAGUGGAUUCCGCCGCGAAGGCGGUUUCCGGCUUGCUUCCUCAACCCUGGCAGU

GGCUCUUUAAAGGCGGCUGGUUUUUCCUGAAAAGAAUUGCCAACCGGAAACCUG

UUGGCGCUGCCAGUGUGGCGGGUGAACCUGAUGGAGGUGAGGUGACCUUCCGCG

UAUACGCUAGUAUCGCGGAUGCCCAGAAUGAUGUACCCUGUAUCGCCAGCUCGGC

GGCCUCUACUCAAUCCAUACAGACGGAGGGGCUCAAGAUUUCCCAGGUGACUCCU

GGGACCAUUGGCAUGCCUGAAACUGCAAUUGCCACACAUAAUAUGGUCCCACCAC

CCGAGUCCGGACCCUACUACUAUCAGGGGCCCACCUGGAGGCUGCUAUUCCCUU

GCGCGGCCCCAAGUAUACACAGUGGAUUCUUGUGGAUGCCGGACGCUCCCAGGAA

UCGGCCCGCCUCCAUUCCGGGGUGGUCCCGGCAGAGCAGACCUCGGCCUGGUCGA

GCUGUACCUUGGAACUCCCAGGCACUUUCCUCCAGAAUAUGCAUGAGAUUGAUCC

CCGUGAUGUUGCAGCCGGUACCUUUCCCAUCAACUACUGGAAUGCGAGCACCUCG

ACGCUCACGCGGCUCGGUACCGCCUACGGUUGCAAUCAAGCGCGGGCACGCACCU

AUGGGGAGGGAGUCCCGCAUGUGGUCAUCUCCACCACCUCUGUCCUCUGGAGGGC

CGAUGUCUCCGAAGGGUGGAACUAUGACAACUUUGUAGCUGCCAUCGGAAUCC

UAUUGUGGAGGCUGGGCCUAAUGUCCAUGGAACCGAACAGGGCAUGCCUCUUACC

-continued

CGUGGCACUCUCAACUGGCCCGGAGGCGAUAGGAAUCGCUGGCCCUACCGCAACC

AGAUUGAGGAGGGUCGCUGGUACGUGACCUUCUGGACUCAGUACGAUCCUGAUG

AGUGGGUCUGGUUGGAUGAGUUCCAUCUUCAGUUCACCUUGCAGCCGGGCACGCA

UGCCCCUACCGAUAACCAUCACUGGGAUAUAACAACAGAUAGUCUAGGUACUGGC

CUCUGGGGCCUCCGGGAUCUUGUGUUCUACCCAAUAGGUGUUCAGCCCAGGAUAG

UGAUACCCCCACUGGGCCUACCAGCUCCCGUGUGACCUUCGACCUCCCCUCGGG

UGAGGACGAUGAGUACUACACAGAUGAGGAAGGCGAGUCCGAUGAGGGAGCUGA

GGAUGAUGAAGGACCCCCCUUGAAUUUGACCACCCAUUAGACGGCGAUCUCUCG

CAACCCCCCGCCGCCGUCUUGAAAGAUCUGACCUACAAGGGGCGCAAUCUCGCCA

AUGAGUUGUGGAGUACGGGGGUGCCAGAUGCGAAGGCCUGGCUGGCGGGACAGA

CCGUUGACCCGUCGCCAUCCUUUCGCCGCUGGCGGGAGACUUUUCAAAAAGCGCU

CCAGCGUGGUGUGAAACCCCUGGAAGCGCGUGAGCUCGCUACUAGCGAGUUCCUU

GCUCAAAGAGAAAGCCGCGGCCACGCCGAGUAGGAUCGAGGGUACAGCUUUCUCC

CCUUGCUUUCUGCUUCUUUCUGUGCUUUGGUGUUACUUUAGGGUGAUAUAAUU

GGCAUAAAAAUUGGCAAAAAAAAAAAAAAAAAAAA

>Mouse_Astrovirus_STL_CY3_20120618_Partial
(SEQ ID NO: 3)
CUUUGGAGGGUGGACCAAAAGCUGUUCAUGGCUAAGGCCAAACAACAACAGAA

AAAUGCUACGACCGUCACCACUACAACUGUUUCUGGUGGCAGUGGUCGGCGGUCU

CGCAGGCGCGCUGUACGGCGCCGCGCUGCAGGCUCUUCUAACCCCUCAACAAAGA

CAACAACUGUUCGGACUGUUUUUCGCCGCAAUACCCGGCCUCGCGGUAAUCGCCG

CAGGAGUAGGAAUGCUCAGCGGCAGACUCCUCGCGAGGUUGUCCAGACGGUUACG

GCGACCCUCGGAACGGUGGCGCGAACCAGGGCGAUCAGGUCGAGCUUGAGAUGG

CAGCGCUCCUCAGCCCAGCGCUGAUCAAGGAAACAACUGGCUCAAAUGCAUUUGG

UCCACUACAGAUGUAUGCCUCCACGCAUGCCAUGUGGAGGGUGGAUAGGCUCACA

CUCAAGCUCACCCCCUUGGUCGGCGCCUCCGCCGUCUCCGGUACAGCAGUUCGUG

CCUCACUGAAUAUGACAUCAGGACCCGCUGCGCCCGCCUGGUCAGCUCUGGGCGC

GCGGAAGCACGUGGAUACCAACCCUGGUCGGUCGGCCUCCUUCACCCUCACAGCC

GCCGACAUCCCUGGCCCUAAGCAAGGUUGGUUCCUCACUAACACCAAGCAAGACG

CCGGCUUCUCAGUCGGCGGGGCCAUUGAGAUCCAUACUCUCGGCAAGACAAUGUC

AACCUACCAGAAUGCGCCCUACACCGGCCCACUCUUUCUUGCCGAGGUCACAGGC

ACCUGGAGGUUUAAGAACUAUGAGCCCCAGCCUGGCAUGCUUAACCUCCUCAAGA

CCGAGGUUAAAGAGCCUGCGGGCACUGUGAAAGUACACUCAAAGCCCGGGGAGCC

UGUCACACUCUCUAUUCCUGAAGCAGGGACCUUUGCCGGCCUUGAGAGGCUAAAU

CCAACAGCUUCGGCCACGCCGGGUGAGAUCAUCUGGGAGGUGGUGGACUCCGCCG

CGAAUGCGGUCUCCGGACUACUCCCUCAACCCUGGCAGUGGCUCUUUAAAGGCGG

CUGGUUCUUCCUGAAAAGGAUUGCCAACCGGAAACCGGUUGGUGCUGCUACUGU

GGCGGGUGAACCUGAUGGAGGUGAAGUUACCUUCCGCGUCUAUGCCAGCAUCGCG

GAUGCCCAGAAUGAUGUUCCUUGCAUUGCUUCCUCGCAGGCCUCUACUCAAUCCA

UACAGACGCAGGGGCUUAAGAUCUCUCAAGUGACUCCUGGGACCAUUGGCAUGCC

CGAAACCGCGAUUGCCACCCAUAAUAUGGUCCCACCACCUGAGUCUGGACCCUAC

-continued

UACUAUCAGGGGCCCACCCUGGAGGCUGCUGCUCCCCUGAAAGCCCCCAAAUACA

CACAGUGGAUACUUGUGGACGCUGGGGCUUCCCAGGAGGGGCCUCGCCUACACUC

CGGGUGGUUCCAGCAGAGCAGACCUCAGCCUGGUCGAGCUGCACCUUGGAGCUC

CCAGGCACCUUCCUCCAGAACAUGCAUGAGAUUGACCCCCGUGACGUUGCAGCCG

GUACCUUUCCCAUCAAUCACUGGAAUGCGAACACUUCGGUGCUCACGCGGCUUGG

CACCGCCUACGGUUGCAACCAAGCGCGGGUUCGCACCUCCGGGGAAGUCACGCUG

GUUAUCUCCACCACUUCUGUUCUCUGGAGGGCCGAUGUCUCCAUAGGGUGGAACU

AUGACAACUUCCUAGCUGCCAUCUGGUGCCCCAUUGUGGUGGCUGGGCCUGGUGU

CCAUGGAACUGAACAGGGCAUGCCUCUUACCCGGGGCACUCUCAACUGGCCCGGG

GGCGAUAGGAAUCGCUGGCCCUACCGUAACCAGAUUGAGGAGGGUCACUGGUAU

GUGACCUUCUGGACUCAGUACGAUCCUGAUGAGUGGGUCUGGUUGGACGACUUC

CACCUCCAGUUCACCUUGCAACCGGGCACGCAUACCCCCACUGAUAACCACCGCU

GGGAUAUAACAACAGAUAGCUUGGGCACUGGCCUCUGGGGCCUCCGGGACCUUGU

GUUCUACCCAAUAGGUGUUCAGCCCAGGAUAGUGAUACCACCCACUGGGCCUACC

AGCUCCCGUGUGGUCUUCGACCUCCCCUCGGGUGAGGACGAUGAGUACUACACAG

AUGAGGAAGGCGAGUCCGAUGAGGGAGCUGAGGAUGAUGAAGGAAACCCCCUUG

AUUUUGACCACCCAUUAGACGGCGAUCUCUCGCAACCCCCCGCCGCCGUCUUGAA

AGAUCUGACUUAUAAGGGGCGUAAUCUCGCCAAUGAGUUGUGGAGUACGGGGGU

GCCAGAUGCGAAGGCCUGGUUGGCGGGACAAGCCGUUGACCCGUCGCCAUCCUUU

CGCCGCUGGCGGGAGACCUAUCAAAAAGCGCUCCAGCGUGGUUUGAAACCCCUGG

AAGCGCGUGAGCUCGCUACUAGCGAGUUCUUGCUCAAAGAGAAAGCCGCGGCCA

CGCCGAGUAGGAUCGAGGGUACAGCUUUCUCCCCUGCUUUUCUGCUUCUUUCUGU

GCUUCUGGUGUUACUUUAGGGUGAUAUAAUUGGCAUAAAAAUUGGCAAAAAAA

AAAAAAAAAAAAAAAAAAAAAAAAAAAAA

>Mouse_Astrovirus_STL_CY4_20120618_Partial
(SEQ ID NO: 4)
CUUUGGAGGGUGGACCAAAAGCUGUUCAUGGCUAAGGCCAAACAACAACAGAA

AAAUGCCACGACCGUCACCACUACAACUGUUUCUGGUGGCAGUGGUCGGCGGUCU

CGCAGGCGCGCUGUACGGCGCCGCGCUGCAGGCUCUUCUAACCCCUCAACAAAGA

CAACAACUGUUCGGACUGUUUUUCGCCGCAAUACCCGGCCUCGCGGUAAUCGCCG

CAGGAGUAGGAAUGCUCAGCGGCAGACUCCUCGCGAGGUUGUCCAGACGGUUACG

GCGACCCUCGGAACGGUUGGCGCGAACCAGGGCGAUCAGGUCGAGCUUGAGAUGG

CAGCGCUCCUCAGCCCAGCGCUGAUCAAGGAAACAACUGGCUCAAAUGCUUUUGG

UCCACUACAGAUGUAUGCCUCCACGCAUGCCAUGUGGAGGGUGGAUAGGCUCACA

CUCAAGCUCACCCCCUUGGUCGGCGCCUCCGCCGUCUCCGGCACAGCAGUUCGUG

CCUCACUGAAUAUGACAUCAGGACCCGCUGCGCCCGCCUGGUCAGCUCUGGGCGC

GCGGAAGCACGUGGAUACCAACCCUGGUCGGUCGCCUCUUUCACCCUCACAGCC

GCCGACAUCCCUGGCCCUAAGCAAGGUUGGUUCCUCACUAACACCAAGCAAGACG

CCGGCUUCUCAGUCGGCGGGGCCAUUGAGAUUCAUACUCUCGGCAAGACAAUGUC

AACCUACCAGAAUGCGCCCUAUACCGGCCCACUCUUUCUUGCCGAGGUCACAGGU

ACCUGGAGGUUUAAGAACUAUGAGCCCCAGCCUGGCAUGCUUAACCUCCUCAAGA

CCGAGGUUAAAGAGCCUGCGGGCACUGUGAAAGUACAUUCAAAGCCCGGGGAGCC

-continued

```
UGUCACACUUUCUAUUCCUGAAGCAGGGACCUUUGCCGGCCUUGAGAGGCUAAAU
CCAACAGCCUCGGCCACGCCGGGUGAGAUCAUCUGGGAGGUGGUGGACUCCGCCG
CGAAUGCGGUCUCCGGACUACUCCCUCAACCCUGGCAGUGGCUCUUUAAAGGCGG
CUGGUUCUUCCUGAAAAGGAUUGCCAACCGGAAACCGGUUGGUGCUGCUACUGU
GGCGGGUGAACCUGAUGGAGGUGAAGUUACCUUCCGCGUCUAUGCCAGCAUCGCG
GAUGCCCAGAAUGAUGUUCCUUGCAUUGCCUCCUCGCAGGCCUCUACUCAAUCCA
UACAGACGCAGGGGCUUAAGAUCUCUCAAGUGACUCCUGGGACCAUUGGCAUGCC
CGAAACCGCGAUUGCCACCCAUAAUAUGGUCCCACCACCUGAGUCUGGACCCUAU
UACUAUCAGGGGCCCACCCUGGAGGCUGCUGCUCCCCUGAAAGCCCCCAAAUACA
CACAGUGGAUACUUGUGGACGCUGGGACUUCCCAGGAGGGGCCUCGCUUACACUC
CGGGGUGGUUCCAGCAGGGCAGACCUCAGCCUGGUCGAGCUGCACCUUGGAGCUC
CCAGGCACCUUUCUUCAGAACAUGCAUGAGAUUGAUCCCCGUGAUGUUGCAGCUG
GCACUUUUCCCAUCAACCACUGGAACGUGCGCACCUCGACGCUUACGCGGCUUGG
CAUCGCCUAUGGCUGUAAUCAGGCGCGGGUCCGCACCUAUGGGGAAGGGGUCCCG
CAUGUGGUCAUUUCCACCACCUCUGUGCUCUGGAGGGCCGAUGUCUCCGAAGGCU
GGAACUAUGACAACUUUCUUGCUGCCAUCUGGAAUCCCAUUGUGGAGGCUGGGCC
CUCCACCCAUGGAACUGAACAGGGUGUGCCUCUUACCCGGGGCACUCUCAACUGG
CCCGGGGGUGAUAGAAAUCGCUGGCCCUACCGCAACCAGGUUGAGGAAGGUCACU
GGUACGUGACCUUCUGGACUCAGUACGAUCCUGAUGAGUGGGUCUGGUUGGAUG
AGUUCAAUCUCCAGUUCACCUUGCAGCCCGGCAACCACACCCCUACUGCUAACCA
CCACUGGGAUAUAACAACAGAUAGCUUAGGCACUGGCCUCUGGGGCCUCCGGGAC
CUUGUGUUCUAUCCAAUAGGUGUCCAGCCCAGGAUAGUGAUACCGCCUACUGGGC
CUACUAGCUCCCGUGUGACCUUCGACCUCCCCUCGGGUGAGGACGAUGAGUAUUA
CACAGAUGAGGAAGGCGAGUCCGAUGAGGGAGCUCAGGAUGAUGAAGGGAAUCC
CCUUGAAUUUGACCAUCCAUUAGACGGCGAUCUCUCGCAACCCCCCGCCGCCGUC
CUGAAAGAUCUAACCUACAAGGGGCAAAAUCUCGCCAAUGAGUUGUGGAGUACG
GGGGUGCCAGAUGCGAAGGCCUGGCUGGCGGGGCAGACUGUUGACCCGUCGCCAU
CCUUUCGCCGCUGGCGGGAGACCUUUCAAAAAGCGCUCCAGCGUGGUGGUAAAGCC
CCUGGAAGCGCGAGAACUCGCCACCAGCGAGUUCUUGCUCAAAGAGAAAGCCGC
GGCCACGCCGAGUAGGAUCGAGGGUACAGCUUUCUCUCCCCGCUUUUCUGCUCCU
UUUCUGUGCUUUUGGUGUUACUUUAGGGUGAUAUAAUUGGCAUAAAAAUUGGCA
AAAAAAAAAAAAAAAAAAAAAAAAAAAAAAAAAA
```

Oligonucleotides of the present teachings, which include but are not limited to oligonucleotides which can serve as probes and/or primers for detecting a murine astrovirus, include the following non-limiting examples:

(SEQ ID NO: 5)
CUUUGGAGGGGAGGACCAAAAGCUCUUCAUGGGC;

(SEQ ID NO: 6)
CCAAGAAAGAGGCACTAGTGGCACTC;

(SEQ ID NO: 7)
GTTTTTTTTTTTTTTTTTTTTGCCAATTTTTATGCCAATTATATCACC
C;

(SEQ ID NO: 8)
TACATCGAGCGGGTGGTCGC;

(SEQ ID NO: 9)
GTGTCACTAACGCGCACCTTTTCA;
and

TTTGGCATGTGGGTTAA. (SEQ ID NO: 10)

In various aspects, an oligonucleotide can be RNA, DNA or a synthetic analogue such as a peptide nucleic acid. In various aspects, an oligonucleotide of the present teachings can further comprise one or more labels, such as a fluorophore, a fluorescence quencher, a hapten such as biotin, or a radioisotope such as $^{33}$H, $^{14}$C, $^{32}$P, $^{33}$P, $^{35}$S, or $^{125}$I.

Oligopeptides of the present teachings, which include but are not limited to peptides that can serve as antigens for a vaccine, an antibody or a serum conversion assay, or a competitive probe for an antibody-based assay such as a radioimmunoassay include, without limitation, CGGDRNRWPYRNQIE (SEQ ID NO: 11)
and

CSEFLAQRESRGHAE. (SEQ ID NO: 12)

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example demonstrates the detection of astroviruses using next generation sequencing.

In these experiments, to examine the mouse virome in an unbiased manner, fecal RNA and DNA libraries from three immunocompetent C57BL/6 (B6) mice were generated. The fecal RNA and DNA libraries were sequenced using 454 (pyrosequencing) technology (Roche) and VirusHunter was used to analyze the resulting reads. 100 mg of frozen stool was chipped and then resuspended in 6 volumes of PBS (Finkbeiner, S. R., et al., PLoS. Pathog. 4: e1000011, 2008). The sample was centrifuged to pellet particulate matter and the supernatant was then passed through a 0.45 µm filter. Total nucleic acid was isolated from 200 µL primary stool filtrate using AMPLIPREP DNA extraction machine (Roche) according to manufacturer's instructions. To enable subsequent detection of both RNA and DNA viruses, total nucleic acid from each sample was reverse transcribed and amplified as previously described (Wang, D., et al., PLoS Biol. 1: E2, 2003). Briefly, RNA templates were reverse transcribed using primerA containing a 16-nucleotide specific sequence followed by 9 random nucleotides for random priming. The 16-nucleotide specific sequence is unique for each sample and served as a barcode in assigning sequencing reads to a sample. SEQUENASE (United States Biochemical) was used for second strand cDNA synthesis and for random-primed amplification of DNA templates using PrimerA. Each sample was then subjected to 40 cycles of PCR amplification using PrimerB containing the same 16 nucleotide specific sequence as in the corresponding PrimerA. Amplification products were pooled, adaptor-ligated and sequenced at the Washington University Genome Sequencing Center on the 454 GS-FLX platform (454 Life Sciences).

Sequences were analyzed using customized pipeline VirusHunter as described (Zhao, G., et al., J Virol. 85: 10230-8, 2010. Briefly, sequence reads were assigned to samples based on the unique barcode sequences (i.e. PrimerB sequences). For further analysis, primer sequences were trimmed off and the sequence reads were clustered using CD-HIT (Li, W., and Godzik, A., Bioinform. 22: 1658-9, 2006) to identify redundant reads. Sequences were clustered on the basis of 95% identity over 95% sequence length, and the longest sequence from each cluster was picked as the representative sequence. Then, unique sequences were masked by REPEATMASKER (Institute for Systems Biology). If a sequence did not contain a stretch of at least 50 consecutive non-"N" nucleotides or if greater than 40% of the total length of the sequence is masked, it was removed from further analysis (i.e., "filtered"). Good quality sequences after filtering were sequentially compared against (i) the human genome using BLASTn; (ii) GenBank nt database using BLASTn; (iii) GenBank nr database using BLASTx (Altschul, S. F., et al., J. Mol. Biol. 215: 403-10, 1990); Minimal e-value cutoffs of 1e-10 and 1e-5 were applied for BLASTn and BLASTx, respectively. Sequences were phylotyped as human, mouse, fungal, bacterial, phage, viral, or other based on the identity of the top BLAST hit. Sequences without any significant hit to any of the databases were placed in the "unassigned" category. If a sequence aligns to both a virus and other kingdom (e.g. bacteria or fungi) with the same e value it is classified as "ambiguous". All eukaryotic viral sequences were further classified into viral families based on the taxonomy ID of the best hit.

All viral sequences and unassigned sequences from each sample were assembled into contigs using NEWBLER (454 Life Sciences) with default parameters. Sample 31H_B6_CR6 and 31H_B6_untreated were sequenced twice. Both sequencing data from each sample were used to try to obtain the best assembly.

132 astrovirus sequences were identified: 21, 76, and 35 from mouse A, B, and C, respectively. No other viral reads were identified. The viral and unassigned reads detected in the feces of mouse B were used to assemble a 6,748-nucleotide (nt) contig with 9-fold coverage. A BLASTn (Altschul, S. F., et al., J. Mol. Biol. 215: 403-10, 1990) search of the NCBI nt database identified this contig to be a highly divergent astrovirus with at most 60% amino acid identity to Human Astrovirus 6 isolate Katano (FIG. 1). Reads detected in the feces of mouse C were used to assemble four contigs ranging from 288 to 3095 nt with 99.0-99.7% nt identity to the 6,748-nt contig from mouse B. Reads detected in the feces of mouse A were used to assemble three contigs ranging from 1024 to 2463 nt with 89.1-95.2% identity to mouse B contig00001 (FIG. 1). These data show the presence of at least two unidentified astroviruses in a specific-pathogen free research facility.

Example 2

This example illustrates the generation and sequencing of full-length murine astrovirus genomes.

Figure 2:
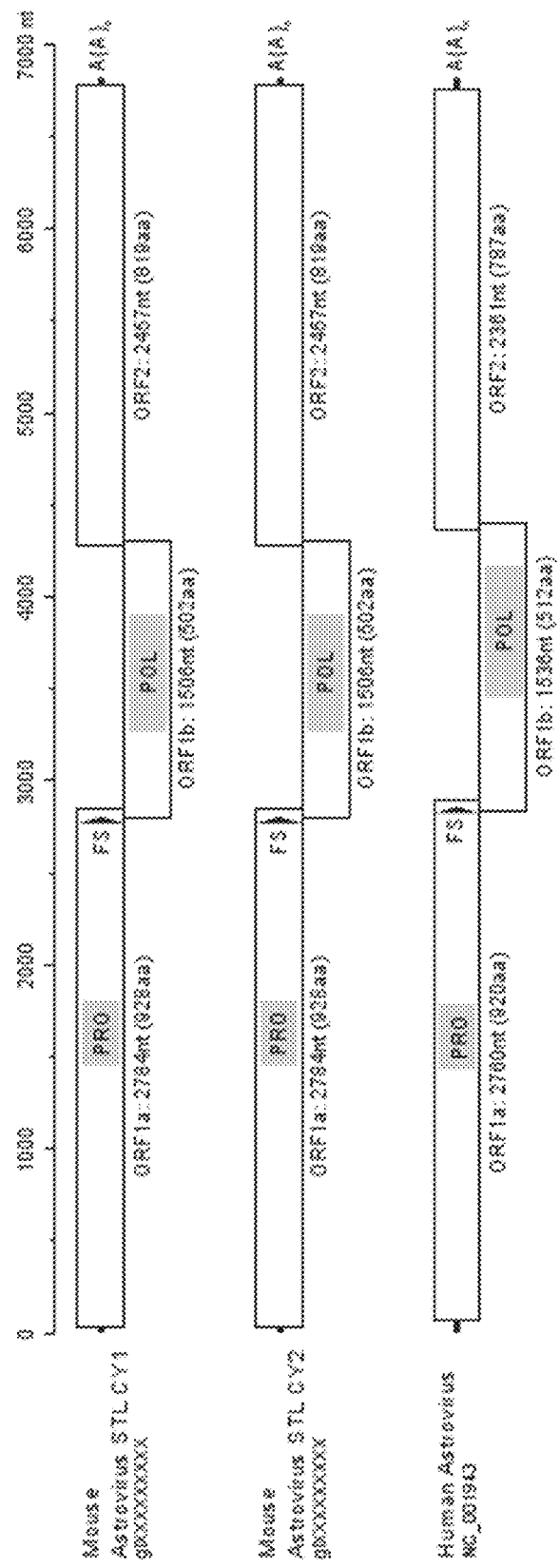
FIG. 2 illustrates a schematic of the identified astrovirus genomes.

In these experiments, subsequent analysis of the fecal specimens from mouse B and mouse C utilizing rapid amplification of cDNA ends (RACE) reactions and traditional Sanger sequencing generated the complete consensus genomes of the two mouse astroviruses: MoAstV STL CY1 and MoAstV STL CY2 (FIG. 2).

Total RNA was extracted from the murine stool samples previously used in the deep sequencing reaction using an RNEASY mini kit (Qiagen, Valencia, Calif.). One microgram of RNA was used as the template for Rapid Amplification of cDNA Ends (RACE) reactions to generate the 5' and 3' genome ends using 5' RACE and 3' RACE kits (Invitrogen, Carsbad, Calif.) according to the manufacturer's instructions. To generate full genomic sequences, one microgram of RNA was used as the template for cDNA synthesis using the SUPERSCRIPT III first-strand synthesis kit and an oligo(dT)$_{12-20}$ primer (Invitrogen) according to the manufacturer's instructions. Full genomic sequences were then amplified using ELONGASE Enzyme Mix (Invitrogen) and primers 5'-CCAAGAAAGAGGCACTAGTG-GCACTC-3' (SEQ ID NO:6) and 5'-GTTTTTTTTTTTTTTTTTTTTTGCCAATTTTTATGC-CAATTATATCACCC-3' (SEQ ID NO:7). The 6.7 kb PCR product was gel purified and ligated into a pCR4-TOPO TA sequencing vector (Invitrogen). Universal M13 forward and reverse primers were used for sequencing, and primer walking was applied as needed. Four clones with 2 to 4-fold redundancy each were used to construct consensus sequence 1 using GENEIOUS Pro v5.0 (Biomatters Ltd.) (Bosma, M. J., and Carroll, A. M., Ann. Rev. Immun. 9: 323-50 m 1991). Three clones with 2 to 4-fold redundancy each were used to construct consensus sequence 2. Predicted ORFs were identified using GENEIOUS. Protein motifs were predicted using Pfam (Finn, R. D., et al., Nuc. Acid. Res. 38: D211-D222, 2010).

Comparison of the MoAstV STL CY1 genome to contig B1 generated by 454 pyrosequencing showed 99.9% nt identity, demonstrating that they are the same virus. Comparison of the MoAstV STL CY2 genome to contigs A00001, A00002, and A00010 generated by 454 pyrosequencing showed 99.6-99.9% nt identity, demonstrating that they are the same virus.

Example 3

This example illustrates that the MoAstV STL genome organization is consistent with other mamastroviruses.

In these experiments, the complete genome length of MoAstV STL CY1 and MoAstV STL CY2 was 6,817 nt, excluding the poly-A tail. MoAstV STL CY1 and MoAstV STL CY2 were predicted to contain a 5' untranslated region (UTR), three open reading frames (ORF 1a, 1b, and 2), a 3' UTR, and a polyA tail¬. The 5' and 3' UTR were determined to be 46 and 90 nt in length, respectively.

ORF1a of MoAstV STL CY1 and MoAstV STL CY2 was predicted to encode a 928 as protein containing a trypsin-like peptidase domain and showed significant similarity to known astroviruses by BLASTP (Altschul, S. F., et al., J. Mol. Biol. 215: 403-10, 1990). The 58-nt ORF1a/1b junction of MoAstV STL CY1 and MoAstV STL CY2 contained the heptanucleotide frameshift signal (AAAAAAC) conserved in all astroviruses (De Benedictis, P., et al., Infect. Genet. Evol. 11: 1529-44, 2011; Jiang, B., et al., P. Natl. Acad. Sci. USA. 90: 10539-43, 1993; Lewis, T. L. and Matsui, S. M., Arch. Virol. 140:1127-35, 1995; Mendez, E. and Arias, C. F., Fields Virology, 5$^{th}$ ed. p. 981-99, 2007). Furthermore FSFinder analysis (Moon, S., et al., Nucleic. Acids. Res. 32: 4884-92, 2004) confirmed that the downstream sequence was capable of generating a stem-loop structure required for a −1 ribosomal frameshift to lead to ORF 1ab translation (Brierley, I., et al., Biochem. Soc. T. 36: 684-9, 2008; Giedroc, D. P. and Cornish, P. V., Virus Res. 139: 193-208, 2009; Mendez, E. and Arias, C. F., Fields Virology, 5$^{th}$ ed. p. 981-99, 2007). The first amino acid in frame with the frameshift signal was predicted to be the start position for ORF1b of MoAstV STL CY1 and MoAstV STL CY2. ORF1b of MoAstV STL CY1 and MoAstV STL CY2 is predicted to encode a 502 as protein containing an RNA dependent RNA polymerase (RdRP) domain, consistent with other astroviruses (De Benedictis, P., et al., Infect. Genet. Evol. 11: 1529-44, 2011; Mendez, E. and Arias, C. F., Fields Virology, 5$^{th}$ ed. p. 981-99, 2007).

MoAstV STL contained a sequence upstream of ORF2—highly conserved among mammalian astroviruses—CUUUGGAGGGGAGGACCAAAAGCUCUU-CAUGGGC (SEQ ID NO: 5), which encompasses the ORF2 start codon (in bold) and is suggested to be a promoter for sgRNA synthesis (Mendez, E. and Arias, C. F., Fields Virology, 5$^{th}$ ed. p. 981-99, 2007; Walter, J. E., et al., Arch. Virol. 146: 2357-67, 2001). As in most other mamastroviruses (De Benedictis, P., et al., Infect. Genet. Evol. 11: 1529-44, 2011), MoAstV STL had an 8-nt region of overlap at the end of ORF1b and beginning of ORF2, with ORF2 maintained in the same frame as ORF1a. ORF2 of MoAstV STL CY1 and MoAstV STL CY2 was predicted to encode an 819-aa protein containing the structural capsid protein.

Collectively, these data demonstrate that the genome organization of MoAstV STL CY1 and MoAstV STL CY2 is consistent with other members of the Astroviridae family, and the mamastrovirus genus in particular.

Example 4

This example illustrates that MoAstV STL viruses are members of a new mamastrovirus genogroup.

In these experiments, to evaluate the relationship between MoAstV STL CY1 and MoAstV STL CY2 and other known astroviruses, phylogenetic analysis was performed using aa sequences predicted to correspond to the capsid-containing ORF2. Analyses performed for ORF1a and 1b showed similar relationships. In all analyses, MoAstV STL clustered with the mamastrovirus genus and not the avastrovirus genus.

Sequences from astrovirus genomic segments encoding ORF1a, 1b, and 2 were translated. These sequences were aligned using ClustalX 2.0.12 (Larkin, M. A., et al., Bioimform. 23: 2947-8, 2007). Phylogenetic inference was performed with maximum parsimony using PAUP 4b10 and maximum likelihood using RAxML (Stamatakis, A., Bioimform. 22; 2688-90, 2006) and BLOSUM62 transition matrix methods with 1000 bootstrap replicates. The resulting phylogenetic trees were visualized using FIGTREE 1.3.1 (Andrew Rambaut), MEGA 5.05 was used for distance estimation (uncorrected p-distance) (Tamura, K., et al., Mol. Biol. Evol. 28: 2731-9, 2011).

The MoAstV STL viruses were most closely related to a clade of recently characterized porcine and wild boar astroviruses, but shared only 33-36% amino acid identity in the capsid region and 63-67% amino acid identity in the RdRp region. This genetic grouping also included the recently deposited mouse astrovirus sequence derived from laboratory mice in Cincinnati, murine astrovirus strain TF18LM but was highly divergent from mouse astrovirus M-52/USA/2008, previously detected in wild mice (Phan, T. G., et al., PLoS Pathog. 7: e1002218, 2011).

In analyses of ORF2, the MoAstV STL viruses formed a distinct genetic cluster with a mean amino acid genetic distance (p-dist) of 0.762±0.010 and 0.789±0.010 to mamastrovirus genogroups I and II, respectively. Intra-group p-dists were 0.548±0.010, 0.629±0.011, and 0.641±0.009 for mamastrovirus genogroups I, II, and the MoAstV STL genetic cluster, respectively.

Collectively, these data demonstrate that MoAstV STL is a mammalian astrovirus and is likely a member of a new third genogroup of mamastroviruses.

Example 5

This example illustrates that adaptive immunity is required to control MoAstV replication.

Figure 3:
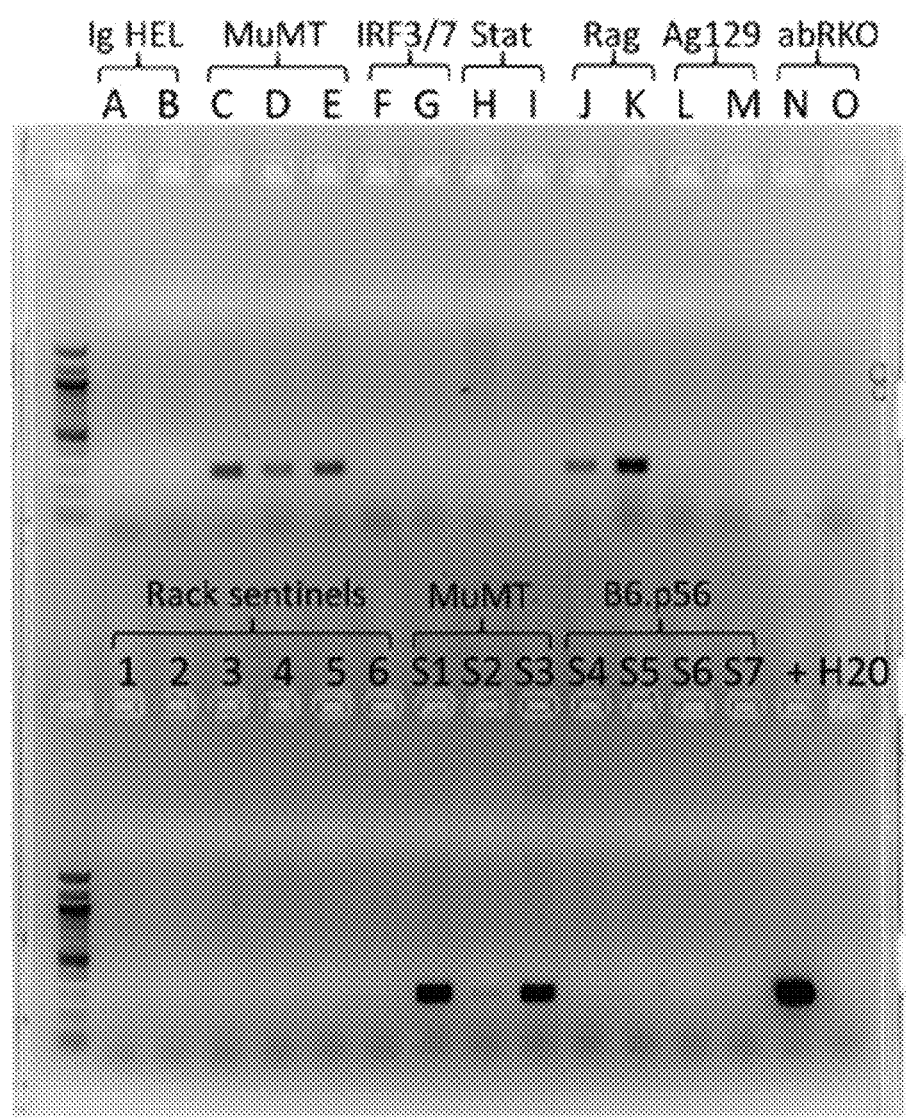
FIG. 3 illustrates detection of astrovirus in immunocompromised mice by PCR.
Figure 4:
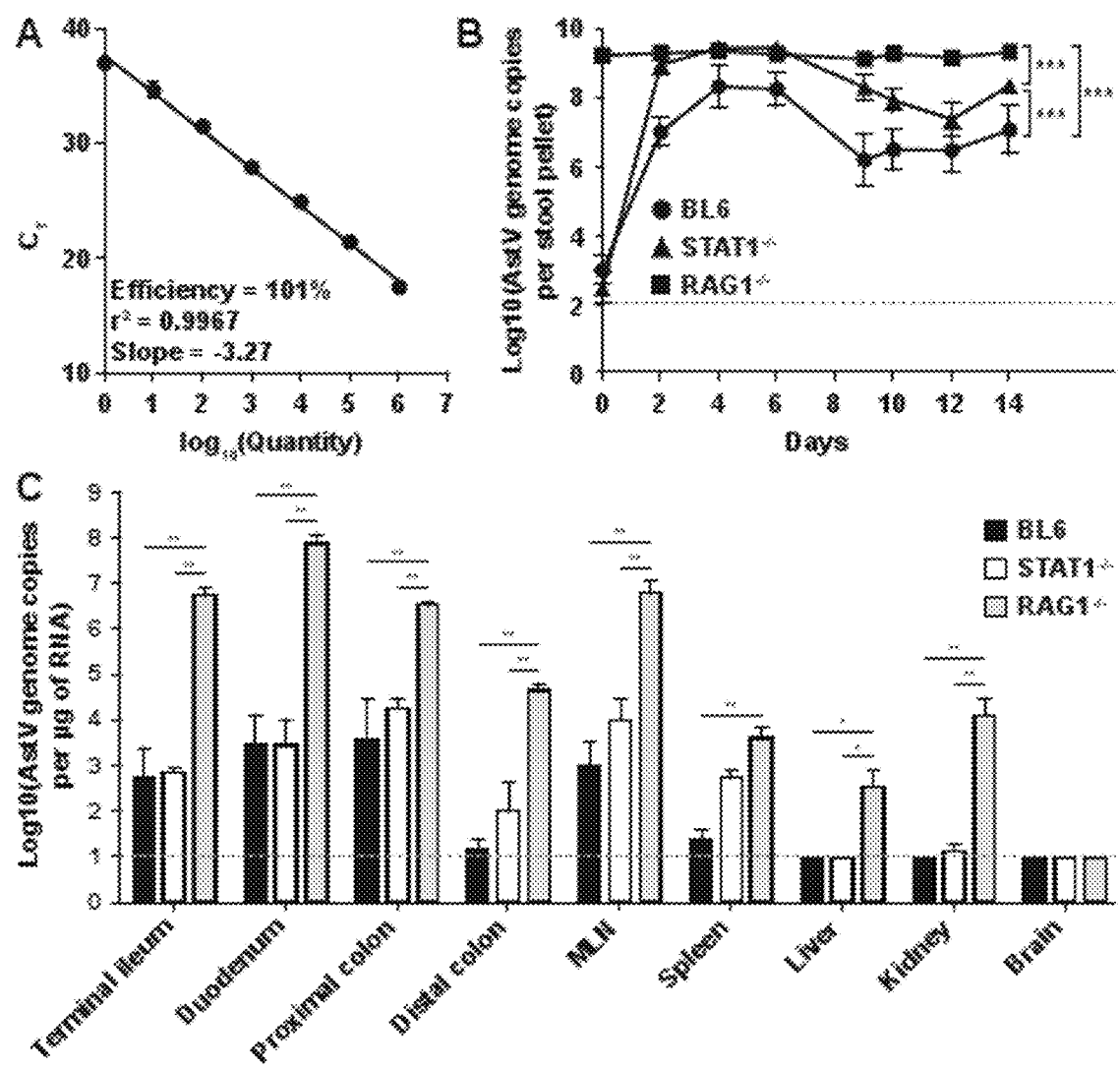
FIG. 4A-C illustrate that adaptive immune response is required to control astrovirus replication.

In these experiments, since MoAstV STL CY1 and MoAstV STL CY2 were originally identified in the feces of asymptomatic B6 mice, whether MoAstV STL was present in the feces of other mice from the same specific-pathogen free research mouse colony was examined. First, astrovirus was detected in immunocompromised mice in the cleanest barrier facility by PCR (FIG. 3). In FIG. 3, B-cell deficient mice are labeled MuMT and RAG deficient mice are labeled B6 RAG. To quantify the number of MoAstV STL CY1 and MoAstV STL CY2 genome copies in tissues and feces, a Taqman-based quantitative reverse transcriptase PCR (qRT-PCR) assay was designed (FIG. 4a), which targeted a 72-bp region of the RdRP conserved between MoAstV STL CY1 and MoAstV STL CY2.

Total RNA was extracted from individual stool pellets using an RNeasy mini kit (Qiagen) or from tissue samples using Trizol reagent (Invitrogen). One tenth of the total stool RNA or 1 µg of tissue RNA was reverse transcribed using ImpromII RT (Promega, Madison, Wis.) and random primers (Invitrogen) to yield cDNA. Triplicate qPCR reactions were performed using one tenth of the cDNA, primers specific to an 80 nt region of ORF1b (sense: 5'-TACATC-GAGCGGGTGGTCGC-3' (SEQ ID NO: 8); antisense: 5'-GTGTCACTAACGCGCACCTTTTCA-3') (SEQ ID NO: 9), and a Taqman probe (Applied Biosystems, Foster City, Calif.) with the sequence 5'-TTTGGCATGTGGGTTAA-3' (SEQ ID NO:10) containing a 5' 6-carboxyfluorescein (6FAM) dye label, 3' nonfluorescence quencher (NFQ) and minor groove binder (MGB). The number of genome copies per sample was determined by comparison to a standard curve (generated by a 10-fold dilution of target-containing-plasmid in tRNA (Invitrogen)). For stool samples, the number of genome copies per sample was multiplied by 100 to account for dilution from total RNA originally extracted from the stool pellet and are reported as genome copies per stool pellet.

Across multiple experiments, the assay was able to repeatedly detect from $10^6$ to $10^1$ genome copies, and 1 genome copy was detected in 2 of 3 technical replicates consistent with Poissan distribution statistics, suggesting that this assay was both sensitive and robust.

Given that previous human studies have implicated the adaptive immune system as essential in the control of astrovirus pathogenesis (Wood, D. J., et al., J. Med. Virol. 24:435-44, 1988), the number of astrovirus genome copies were measured in the feces of mice deficient in B and T cells due to a mutation in Recombination Activating Gene 1 [RAG1, (Mombaerts, P., et al., Cell. 68: 869-77, 1992]. While these mice exhibited no overt signs of illness, up to $10^9$ astrovirus genome copies per fecal pellet were detected and notably, 21/21 $RAG^{-/-}$ mice screened were positive for astrovirus. These data suggest that adaptive immunity is essential for restricting MoAstV replication.

Example 6

This example illustrates that innate and adaptive immunity contributes to the control of MoAstV replication.

In these experiments, to assess the relative hierarchy of innate and adaptive immunity in restricting MoAstV replication, the timecourse of natural astrovirus infection in B6 and $RAG1^{-/-}$ mice were examined, as well as mice deficient in $STAT1^{-/-}$ ($STAT1^{-/-}$). C57BL/6J, B6.$RAG1^{-/-}$, and $STAT1^{-/-}$ mice were bred and housed in an enhanced barrier specific-pathogen-free facility at Washington University in St. Louis in compliance with federal and institutional guidelines (Cadwell, K., et al., Cell. 141: 1135-45, 2010). All studies were performed using age-matched female mice between eight and ten weeks of age. Three mice, one of each genotype, were cohoused on day 0, and fecal samples were collected every 2 days to follow astrovirus shedding. Mice were euthanized on day 14 and tissues were harvested for analysis.

As previous studies have shown that astrovirus infections can spread beyond the gastrointestinal tract (Blomström, A. L., et al., J. Clin. Microbiol. 48: 4392-6, 2010; Quan, P. L., et al., Emerg. Infect. Dis. 16: 918-25, 2010), the distribution of MoAstV was investigated in multiple tissues as well as feces. In order to address the potential presence of additional astrovirus strains that might not be detectable by the TAQ-MAN assay, B6, $STAT1^{-/-}$, and $RAG1^{-/-}$ mice were cohoused for 14 days to ensure infection by the same viruses occurred.

High levels of MoAstV shedding in fecal samples were observed in $RAG1^{-/-}$ mice at day 0 and at all timepoints tested (FIG. 4b). In contrast, low levels of MoAstV were observed in the feces of both B6 and $STAT1^{-/-}$ mice at day 0, prior to cohousing. Two days of cohousing, elevated levels of MoAstV genome copies were detected in feces from B6 and $STAT1^{-/-}$ mice, with $STAT1^{-/-}$ mice shedding significantly more MoAstV than B6 mice at day 2 ($p<0.05$). Overall, MoAstV shedding over the course of the experiment differed significantly by genotype ($p<0.0001$ for all combinations).

The tissue distribution of MoAstV STL was analyzed after 14 days of cohousing. High levels of genome copies in the GI tract of $RAG1^{-/-}$ mice were detected (FIG. 4c), consistent with the observation that $RAG1^{-/-}$ mice shed up to $10^9$ genome copies per stool pellet. The quantity of viral genome copies detected in the GI tract of B6 and $STAT1^{-/-}$ mice were significantly lower than in the $RAG1^{-/-}$ mice ($p<0.001$ for all GI tract tissues tested). While MoAstV RNA was detected in the liver and kidney of $RAG1^{-/-}$ mice, it was not detected in the liver or kidney of B6 or $STAT1^{-/-}$. A limited number of genome copies in the spleen of $STAT1^{-/-}$ mice were detected, twice as many as observed in the spleen of wild-type mice, though this comparison was not statistically significant. MoAstV STL was undetectable in the brain of any mouse tested, in contrast to previously identified enteric mouse pathogens in immunocompromised mice (Karst, S. M., et al., Science. 299: 1575-8, 2003).

These data demonstrate a role for both the innate and adaptive immune systems in the control of astrovirus infection and replication.

Example 7

This example illustrates that MoAstV is present in mice from commercial mouse colonies.

In these experiments, the presence of MoAstV in mice available from commercial vendors was assessed. Since extremely high levels of MoAstV STL in the feces of $RAG1^{-/-}$ mice were previously observed, the present inventors decided to assess the presence of MoAstV STL in commercially available mice lacking B and T cells.

RAG1$^{-/-}$ mice (B6.129S7-Rag1$^{tm1Mom}$/J, cat #002216) were purchased from The Jackson Laboratory, RAG2$^{-/-}$ mice (129S6/SvEvTac-Rag2$^{tm1Fwa}$, cat#RAG2-F) (Shinkai, Y., et al., Cell. 68: 855-67, 1992) from Taconic facility IBU25, and SCID mice (CB17/Icr-Prkdc$^{scid}$/IcrCrl, cat#236) (Bosma, M. J., and Carroll, A. M., Ann. Rev. Immun. 9: 323-50 m 1991) from Charles River facility W09—the three major mouse vendors in the United States. Mice were sacrificed immediately upon arrival and samples were collected for analysis.

Figure 5:
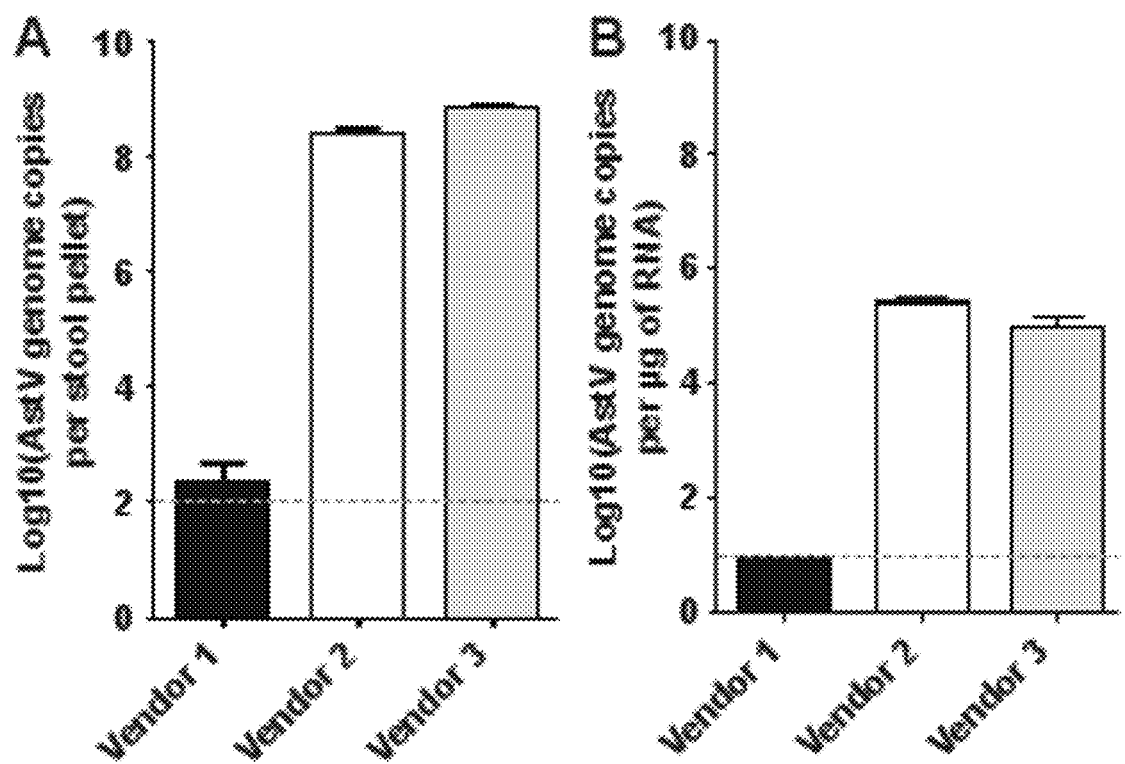
FIG. 5A-B illustrate that astrovirus can be detected in commercially available mice.

Consistent with previous findings (FIG. 4), extremely high levels of MoAstV STL were observed in fecal and tissue samples from RAG1$^{-/-}$ and RAG2$^{-/-}$ mice (FIG. 5). MoAstV was undetectable in the feces or tissues of SCID mice. Overall, however, these data suggest that MoAstV STL is a common pathogen, likely present in many research mouse facilities in the United States.

Example 8

This example illustrates antibody responses during murine astrovirus infection.

Figure 6:
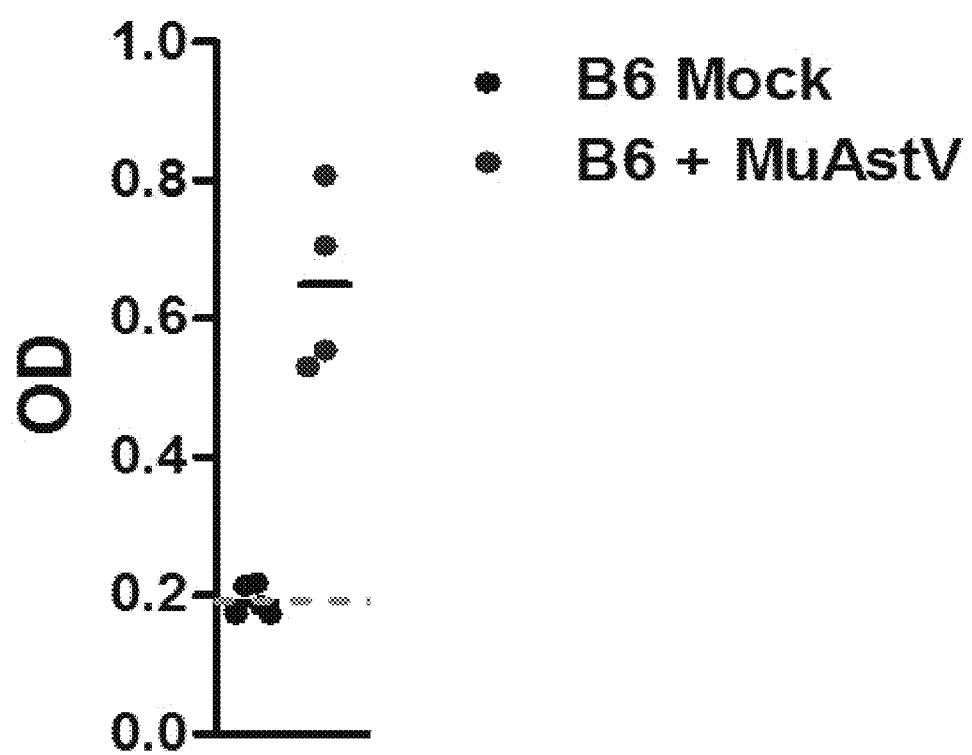
FIG. 6 illustrates antibody responses during marine astrovirus infection.

In these experiments, B6 mice were inoculated with MuAstV or mock-inoculated. Serum antibody responses measured at 16 days. Differences in MuAstV-specific antibodies were observed between MuAstV- and mock-inoculated mice ($p<0.02$; Mann-Whitney test) (FIG. 6).

The astrovirus capsid protein can assemble into virus-like particles (VLP) which share biological properties of virions. A baculovirus system was used to express the capsid protein of MuAstV strain STL 2. The ability of MuAstV VLP to detect serum antibodies specific to MuAstV by ELISA were validated using MuAstV VLP compared to MNV virions, as well as MuAstV and MNV-inoculated mice (data not shown). Using this assay, an elevation of virus-specific antibodies was observed in the serum of MuAstV-inoculated mice compared to mock-inoculated control mice (FIG. 6). These data demonstrate that VLP derived from the sequence of the capsid protein of MuAstV STL2 can detect a serological response to MuAstV infection, which can be used for the establishment of MuAstV-free mice.

Example 9

This example illustrates the prevalence of murine astrovirus in a specific pathogen-free breeding facility.

Fecal pellets were obtained from mice from Dec. 4, 2011-Jan. 15, 2012 and the presence of murine astrovirus tested by quantitative RT-PCR. Limit of detection=100 genome copies/fecal pellet. Mice were housed 1-5 mice/cage, on 7 racks in 1 breeding room. Bedding sentinels were housed 2 mice/cage, 1 cage/rack in the same room.

MuAstV sequences were detected by next generation sequencing or quantitative PCR (qPCR) in the feces of mice from at least six research institutions and two commercial vendors. Furthermore, MuAstV was detected by qPCR in 73% of mouse lines in a single breeding room at Washington University School of Medicine (Table. 1). These results demonstrate that the prevalence of MuAstV in laboratory mice can be equal to or greater than that of murine norovirus (MNV), which is the most prevalent, recognized viral agent in laboratory mice today.

TABLE 1

|  | Mice | | | | Sentinels | |
| --- | --- | --- | --- | --- | --- | --- |
|  | # of mice | # of cages | # of lines | # of racks | # of mice | # of cages |
| MuAstV positive | 122 | 72 | 32 | 7 | 5 | 3 |
| Total tested | 485 | 178 | 44 | 7 | 14 | 7 |
| Prevalence of MuAstV | 25% | 40% | 73% | 100% | 36% | 43% |

Example 10

This example illustrates genetic diversity of murine astroviruses identified by next-generation sequencing.

Virus contigs from fecal samples (red) were aligned with known (black) MuAstV sequences using ClustalW. A maximum-likelihood phylogenetic tree was generated using MEGA.

Figure 7:
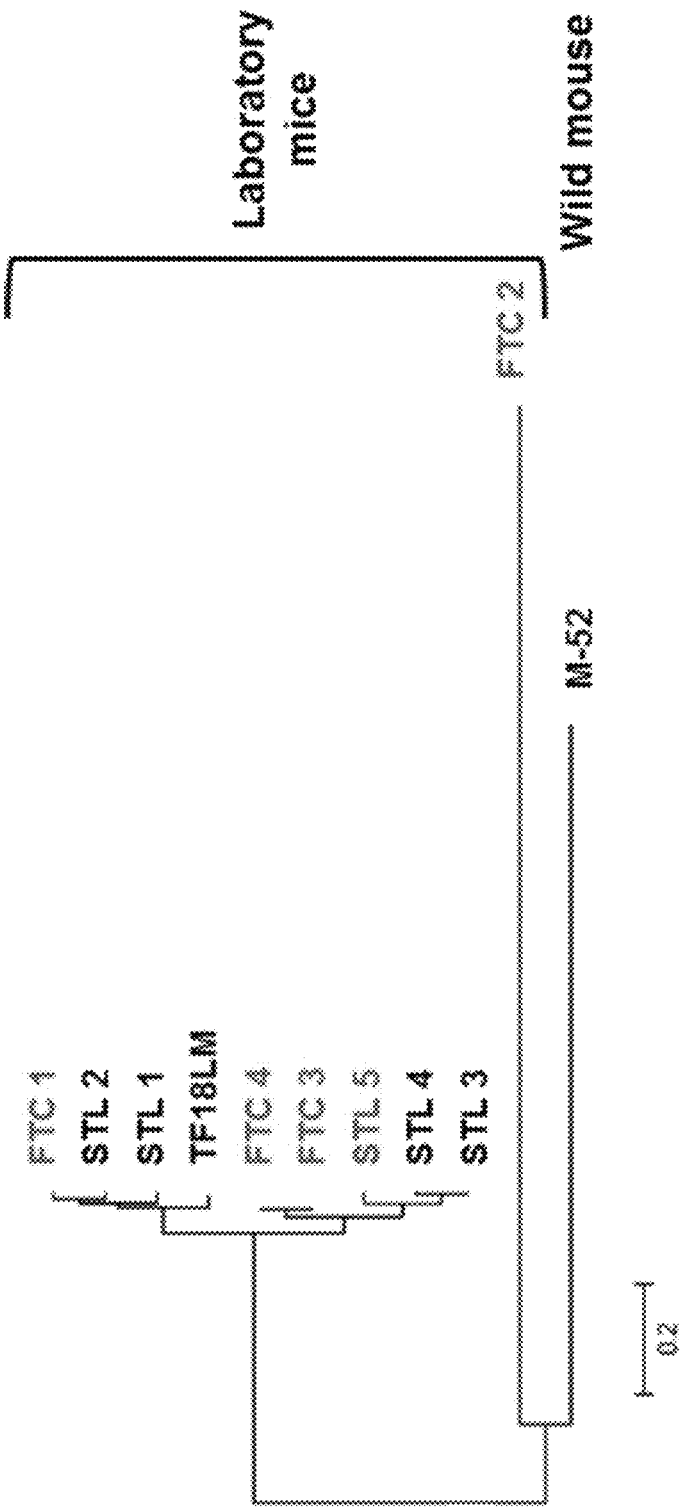
FIG. 7 illustrates genetic diversity of murine astroviruses identified by next generation sequencing.

Shotgun sequencing of libraries of RNA and DNA isolated from 35 fecal samples from laboratory rodents using the 454 GS FLX Titanium platform generated an average of 31,781 high quality reads per sample. The virome was examined using VirusHunter. Sequences with 76-99% nucleotide (nt) identity to MuAstV strain STL 1 were detected in mouse samples (example sequences illustrated in FIG. 7). These data demonstrate that MuAstV can be genetically diverse.

Example 11

This example illustrates kinetics of murine astrovirus shedding.

In these experiments, C57BL/6 (B6) and STAT1$^{-/-}$ mice were inoculated with MuAstV and shedding in feces was measured. RAG1$^{-/-}$ mice were naturally infected with MuAstV and shedding in feces measured for 14 days. Differences in MuAstV shedding were observed between B6 and STAT1$^{-/-}$ mice at 6-12 days ($p<0.05$; one way ANOVA); significant differences in MuAstV shedding were observed between B6 and RAG1$^{-/-}$ mice, STAT1$^{-/-}$ and RAG1$^{-/-}$ mice at all time points ($p<0.05$; one way ANOVA).

Figure 8:
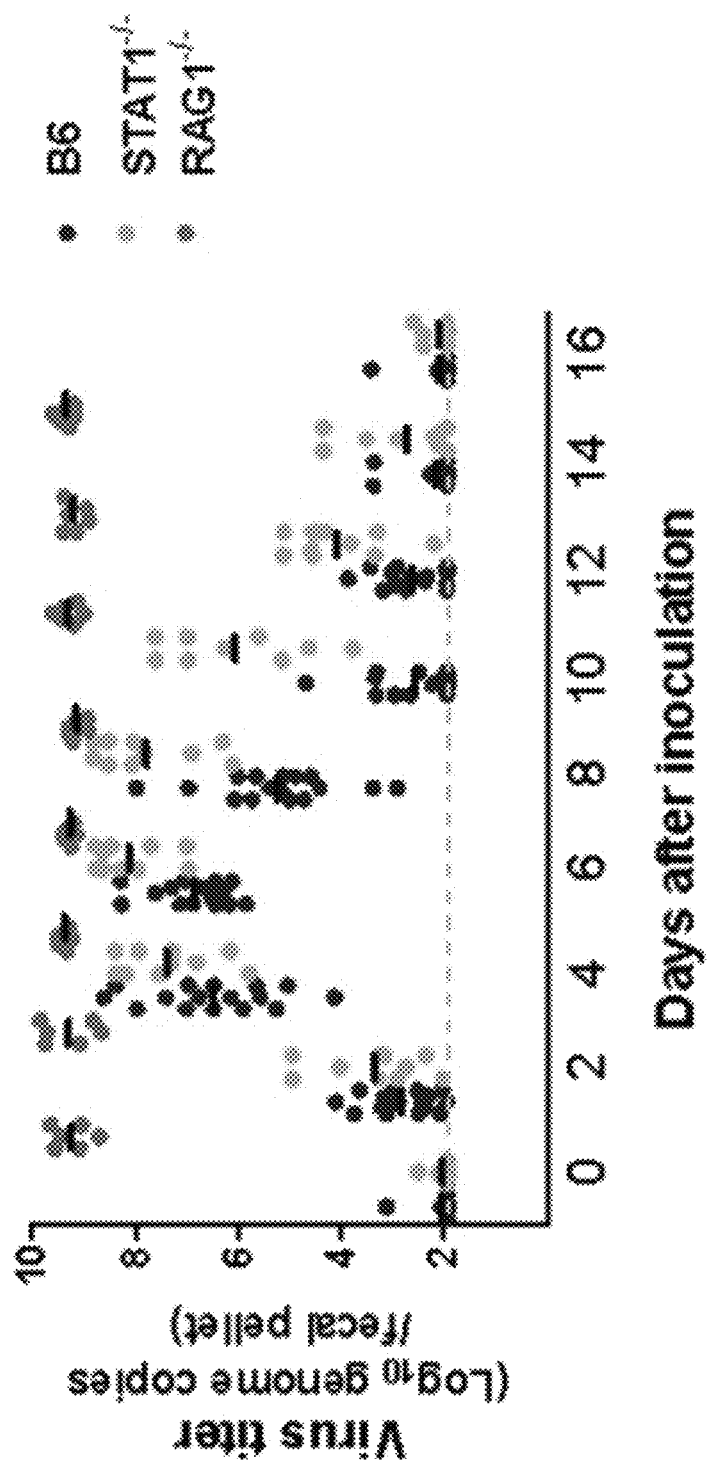
FIG. 8 illustrates kinetics of murine astrovirus shedding.

Experiments using naturally-infected RAG1$^{-/-}$ mice co-housed with B6 and STAT1$^{-/-}$ mice suggest that both innate and adaptive immunity control MuAstV replication. Since the high level, sustained shedding observed in RAG1$^{-/-}$ mice may confound the kinetics of MuAstV replication and clearance in co-housed B6 and STAT1$^{-/-}$ mice, MuAstV shedding in B6 and STAT1$^{-/-}$ mice orally inoculated with a filtered fecal stock of MuAstV containing $5 \times 10^5$ genome copies of MuAstV was re-examined (FIG. 8). Peak MuAstV shedding was reached 6 days after inoculation in B6 and STAT1$^{-/-}$ mice. MuAstV shedding was elevated in STAT1$^{-/-}$ mice compared to B6 mice confirming a role for innate immunity in control of MuAstV replication (FIG. 8). MuAstV shedding declined to baseline in B6 and STAT1$^{-/-}$ mice 16 days after inoculation (FIG. 8), demonstrating that innate immunity can not necessarily be required to control MuAstV clearance.

Example 12

This example illustrates specificity of an ELISA for Astrovirus (AstV) virus-like particles (VLP), and that an ELISA can be used to detect AstV-specific antibodies in mice previously infected with AstV.

Astrovirus VLP generation—The astrovirus capsid protein can assemble into virus-like particles (VLP) which share the biological properties of virions (Moser, L., et. al., J. Virol. 81:11937-45, 2007). To generate virus-like particles, cDNA corresponding to ORF2 of STL CY2 was tagged with a 3' TEV recognition site and 6×His tag and cloned into a pFastBac1 donor vector (Invitrogen) for baculovirus expression. Protein was generated and astrovirus VLPs were purified.

Figure 9:
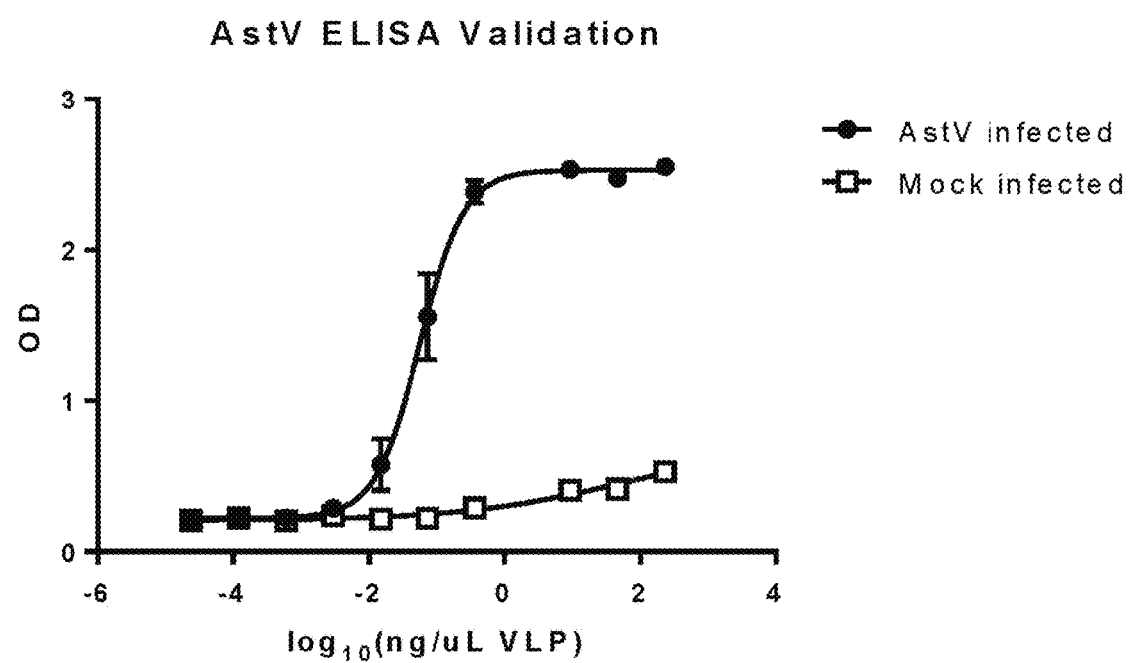
FIG. 9 illustrates an AstV (astrovirus virus-like particles) ELISA validation.

Astrovirus ELISA validation—ELISA plates were coated with serial dilutions of astrovirus VLPs and blocked with 3% BSA prior to use. Serum samples from mock and infected mice were added to the ELISA plate at a 1:100 dilution. Astrovirus VLP-specific antibodies were detected by goat-anti-mouse HRP antibodies (Jackson Immunoresearch) and ABTS peroxidase substrate (ThermoScientific) Signal was detected using a BioRad IMARK microplate reader at 415 nm. Based on the interpolated standard curve (FIG. 9), a concentration of 0.1 ng/L astrovirus VLPs was selected for use in future experiments.

Figure 10:
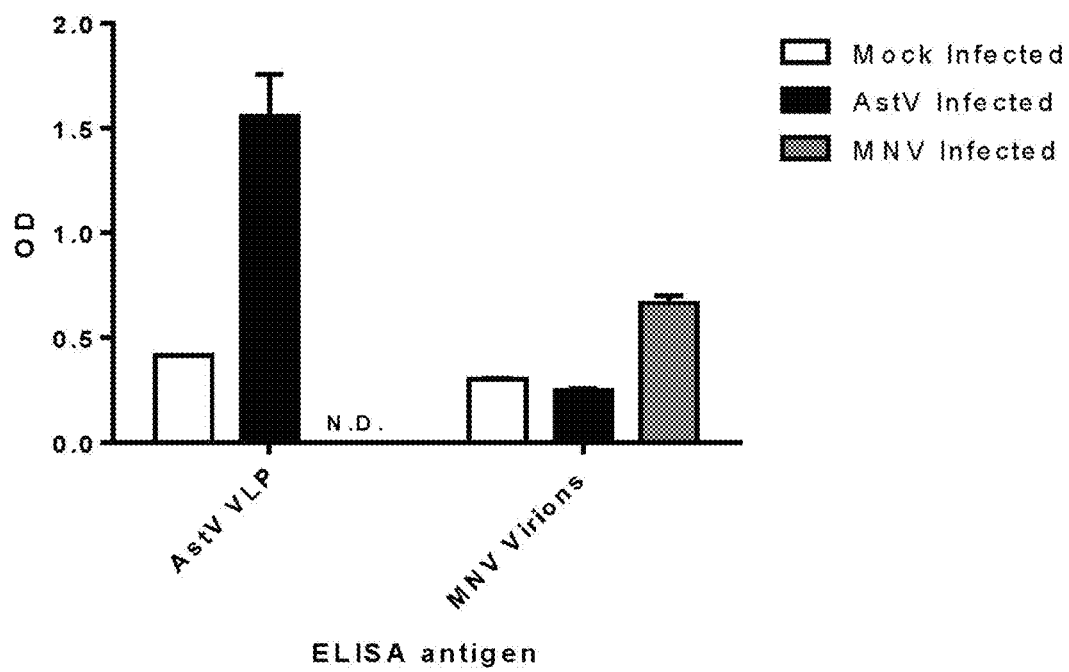
FIG. 10 illustrates a second AstV (astrovirus virus-like particles) ELISA validation.

To further test for specificity, ELISA plates were coated with astrovirus VLPs or UV-inactivated murine norovirus MNV virions. Serum samples from mock, AstV-infected, and MNV-infected mice were analyzed. The data (FIG. 10) validate specificity of the test.

Figure 11:
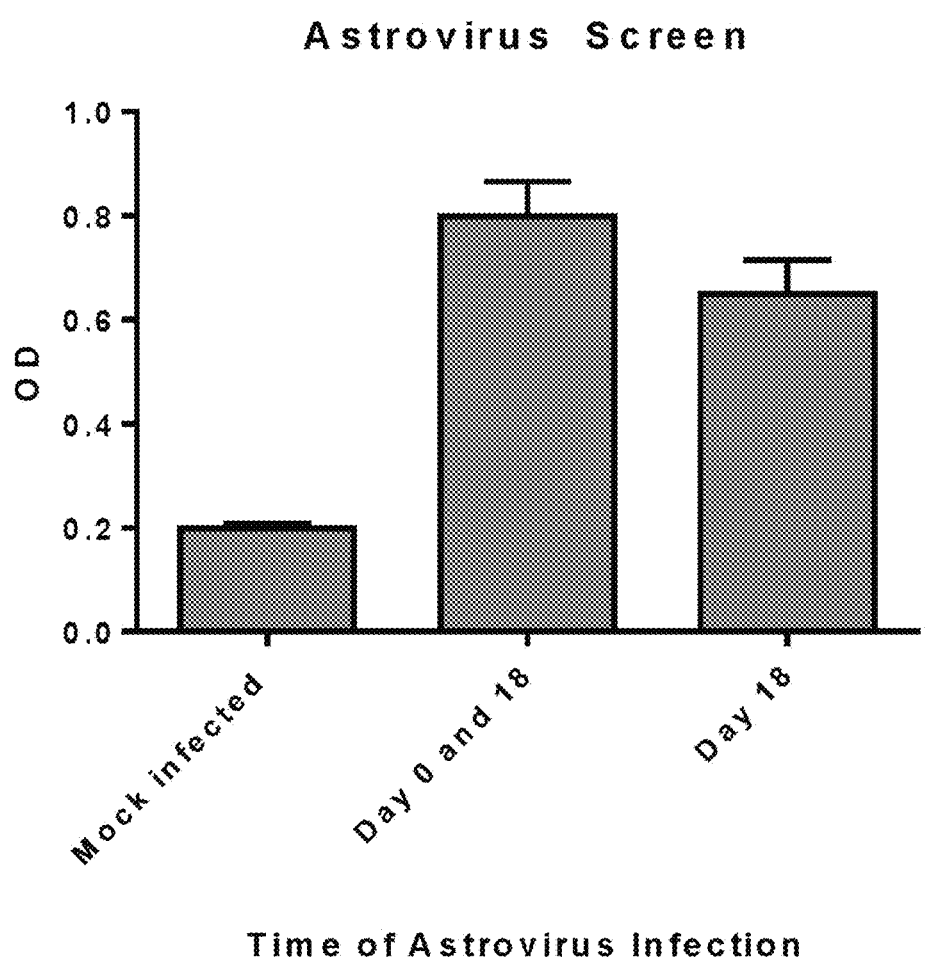
FIG. 11 illustrates an AstV (astrovirus virus-like particles) ELISA screen.

Astrovirus ELISA screen—C57BL/6J mice were orally inoculated on days 0 and/or 18 with 5e5 genome copies of a heterogeneous AstV solution or PBS (mock infected). At day 34 post infection, serum was collected for analysis by ELISA. (FIG. 11). The data illustrate detection of murine astrovirus antibodies by ELISA.

All references cited herein are incorporated by reference, each in its entirety. Applicant reserves the right to challenge any conclusions presented by the authors of any reference.

What is claimed is:

1. A method of detecting the presence, absence or quantity of a murine astrovirus in a mouse sample, the method comprising:
   providing a sample from a mouse comprising or suspected of comprising a murine astrovirus wherein the mouse sample is selected from the group consisting of a fecal sample, a vomitus sample, a tissue sample and a blood sample;
   synthesizing cDNA using sample RNA as a template;
   contacting the cDNA with at least one primer comprising a sequence having at least 95% sequence identity with (SEQ ID NO: 6)
   CCAAGAAAGAGGCACTAGTGGCACTC (SEQ ID NO: 7)
   GTTTTTTTTTTTTTTTTTTTGCCAATTTTTATGCCAATTATATCACCC or (SEQ ID NO: 9)
   GTGTCACTAACGCGCACCTTTTCA;
   and performing a quantitative PCR assay comprising the cDNA and the at least one primer, thereby detecting the presence, absence or quantity of a murine astrovirus nucleic acid.

2. A method of detecting the presence, absence or quantity of a murine astrovirus in a mouse sample in accordance with claim 1, wherein the at least one primer that has at least 95% sequence identity with SEQ ID NO:6, SEQ ID NO:7, or SEQ ID NO:9, has 100% sequence identity with SEQ ID NO:6, SEQ ID NO:7 or SEQ ID NO:9.

3. A method according to claim 1, wherein the sample is a fecal sample.

* * * * *